US010638997B2

(12) United States Patent
Pani et al.

(10) Patent No.: US 10,638,997 B2
(45) Date of Patent: May 5, 2020

(54) ECHO-SCINTIGRAPHIC PROBE FOR MEDICAL APPLICATIONS AND RELEVANT DIAGNOSTIC METHOD

(71) Applicant: UNIVERSITA' DEGLI STUDI DI ROMA "LA SAPIENZA", Rome (IT)

(72) Inventors: Roberto Pani, Rome (IT); Valentino Orsolini Cencelli, Rome (IT); Andrea Fabbri, Rome (IT)

(73) Assignee: Universita' Degli Studi Di Roma "La Sapienza", Rome (IT)

(*) Notice: Subject to any disclaimer, the term of this patent is extended or adjusted under 35 U.S.C. 154(b) by 692 days.

(21) Appl. No.: 15/311,382

(22) PCT Filed: May 14, 2015

(86) PCT No.: PCT/IT2015/000130
§ 371 (c)(1),
(2) Date: Nov. 15, 2016

(87) PCT Pub. No.: WO2015/173841
PCT Pub. Date: Nov. 19, 2015

(65) Prior Publication Data
US 2017/0079609 A1 Mar. 23, 2017

(30) Foreign Application Priority Data

May 16, 2014 (IT) .......................... RM2014A000245

(51) Int. Cl.
*A61B 6/00* (2006.01)
*A61B 8/00* (2006.01)
(Continued)

(52) U.S. Cl.
CPC .......... *A61B 6/5247* (2013.01); *A61B 6/4258* (2013.01); *A61B 8/4416* (2013.01);
(Continued)

(58) Field of Classification Search
CPC ... A61B 6/4258; A61B 6/5247; A61B 8/4416; A61B 8/4444; A61B 8/463; G01T 1/1603; G01T 1/1612
See application file for complete search history.

(56) References Cited

U.S. PATENT DOCUMENTS 4,995,396 A 2/1991 Inaba
6,212,423 B1 4/2001 Krakovitz
(Continued)

FOREIGN PATENT DOCUMENTS

EP 2347791 A1 7/2011
WO 2004042546 A1 5/2004
WO 2014080013 A1 5/2014

OTHER PUBLICATIONS

Huber, J.S. et al., Dual-Modality PET / Ultrasound Imaging of the Prostate, 2005 IEEE Nuclear Science Symposium Conference Record, pp. 2187-2190 (2005).
(Continued)

*Primary Examiner* — Ruth S Smith
(74) *Attorney, Agent, or Firm* — Knobbe Martens Olson & Bear LLP

(57) ABSTRACT

An echo-scintigraphic probe for medical applications and the method of merging images. It is constituted by the union of an ultrasound probe suitably integrated, both in geometric terms, and in terms of image processing, with a scintigraphic probe or gamma camera (3). With a single application of said probe, one is able to provide a double image of the object under examination. The ultrasound probe is housed in the head, above the plane of the collimator and kept projecting to favor the direct contact with the body part of the patient to be examined. The collimator is able to obtain images of the biodistribution of a radiolabelled drug by radiation with frontal incidence, maintaining the characteristics of the ultrasound probe. The probe is applicable to both
(Continued)

clinical diagnosis and intraoperative diagnosis of cancer with the use of radio tracers. A guided diagnostic method is disclosed that realizes a functional integration of a pair of ultrasound and scintigraphic images concurrently obtained by the echo-scintigraphic probe.

9 Claims, 20 Drawing Sheets

(51) Int. Cl.
    *G01T 1/16* (2006.01)
    *G01T 1/161* (2006.01)
(52) U.S. Cl.
    CPC ............ *A61B 8/4444* (2013.01); *A61B 8/463* (2013.01); *G01T 1/1603* (2013.01); *G01T 1/1612* (2013.01)

(56) References Cited

U.S. PATENT DOCUMENTS

2008/0230705 A1  9/2008  Rousso
2009/0030310 A1  1/2009  Hamill
2012/0032086 A1  2/2012  Daghighian

OTHER PUBLICATIONS

International Search Report and Written Opinion for corresponding PCT Application No. PCT/IT2015/000130, 13 pages, dated Nov. 10, 2015.
Pani R .et al., Dual Modality Ultrasound-SPET Detector for Molecular Imaging, Nuclear Physics B (Proc. Supp.) vol. 215, No. 1, pp. 319-323 (2011).
Italian Search Report for ITRM20140245, 9 pages, dated Feb. 2, 2015.

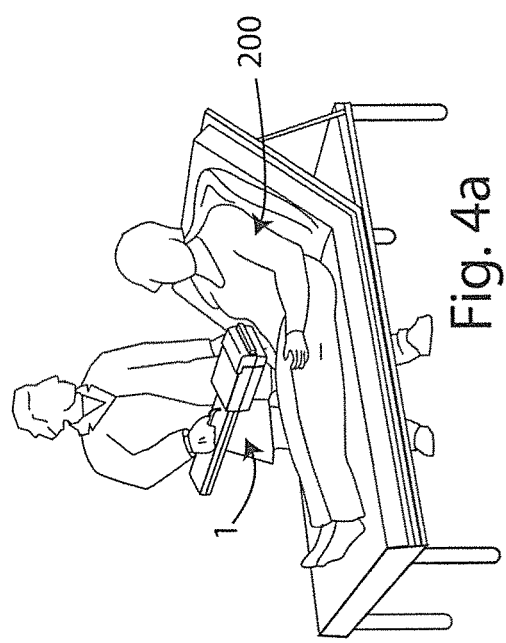
Fig. 4a
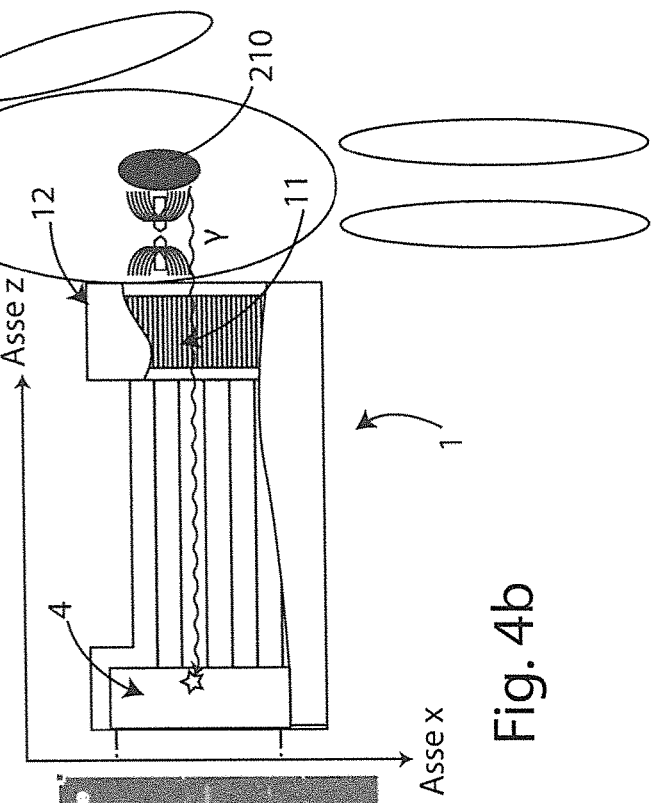
Fig. 4b
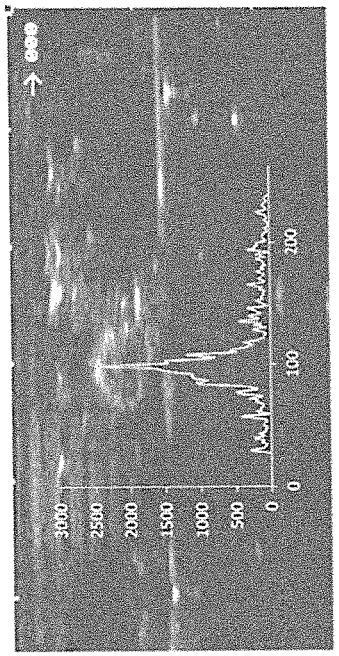

Fig. 13

110: Dimensione immagine gamma G(x,y) 52.6 (x) x 26.2 (y) mm² o 526 x 262 px²

111: Zero immagine angolo in alto a dx Asse x rescente da dx vs sx

112: Traslazione dell'asse x dell'immagine gamma per far coincidere i centri delle due immagini eco-gamma x'= x-a: G (x',y)

113: Suddivisione dell'immagine G'(x',y) in 3 fasce in y, una in campo sonda eco (A) e due fuori campo sonda eco (B e C), dove: A=G'(x',0:n), B=G'(x',n+1:m) e C=G'(x',m+1:261)

114: Proiezione della matrice A in campo con la sonda sull'asse comune X $$A'(x') = \sum_{y=0}^{n} A(x', y)$$

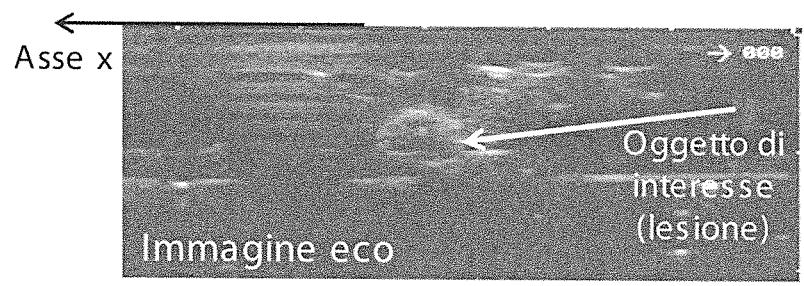
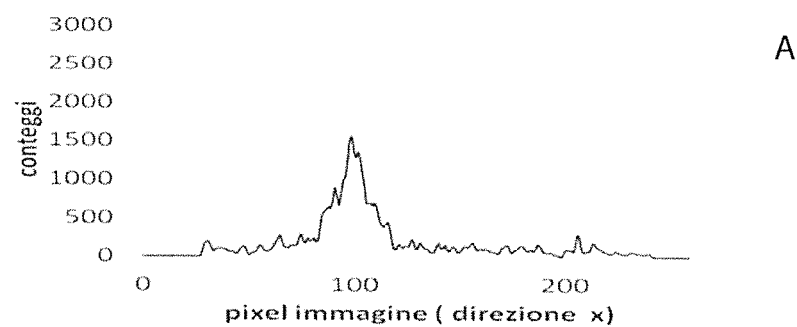
A
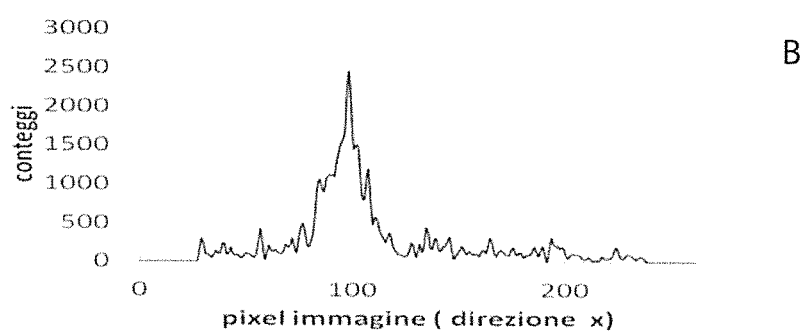
B
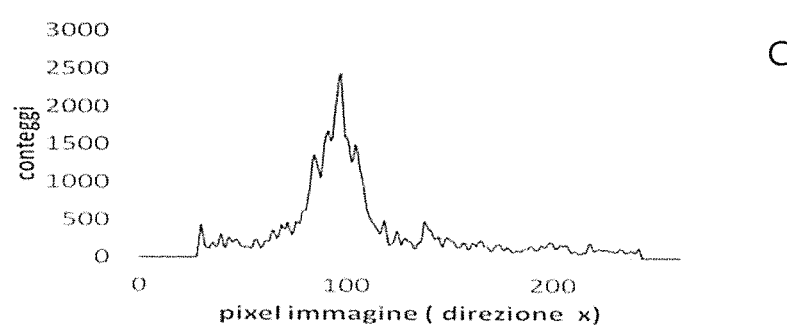
C
Fig. 17

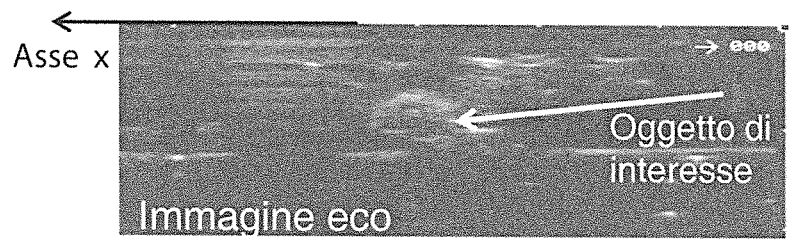
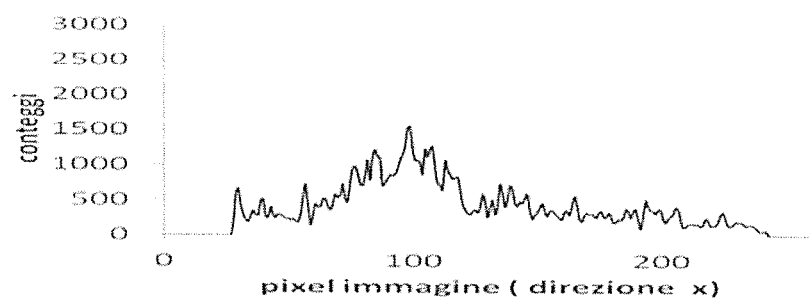
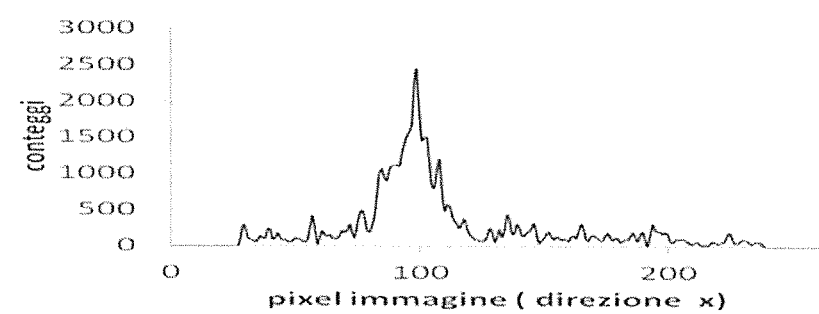
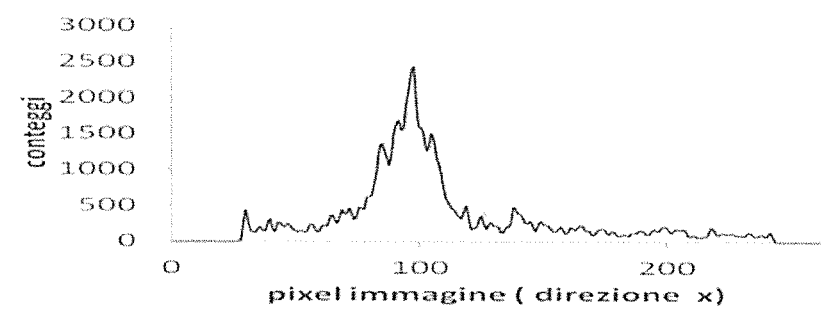
Fig. 19

ECHO-SCINTIGRAPHIC PROBE FOR MEDICAL APPLICATIONS AND RELEVANT DIAGNOSTIC METHOD

FIELD OF THE INVENTION

The present invention relates to an echo-scintigraphic probe for medical and related diagnostic method.

More specifically, the probe according to the invention includes both an ultrasound probe and a scintigraphic probe, assembled in such a way that, in one pass on the area to investigate, it provides two images of the same area which will then be integrated by the method according to the invention, providing a guide to the investigation. It was devised to solve the current problems related to the complexity of the current large and expensive imaging systems in general and in particular for those techniques based on the use of a tomographic ring integrated with at least two detectors, such as SPECT CT, PET CT, CT SNMR and recently PET NMR.

BACKGROUND

In medicine, extensive use of instrumentation is made to obtain images in the diagnosis of diseases.

In particular, both the ultrasound images and the scintigraphic one are used for the secondary diagnosis of those cases for which disease is suspected after previous radiographic examinations.

Recently, several reports have demonstrated the greater diagnostic predictivity of dual "imaging" systems, or detectors capable of providing a double image of the object under examination.

The basic criterion is to combine two complementary images: a morphological image that can provide anatomical details (RX, CT and NMR) with another capable of providing information on the biological functionality (imaging obtained with the use of molecules labeled with radionuclides, termed radio-tracers, such as PET SPECT).

The solution most proposed in the known art is represented by large and expensive systems based on the use of a tomographic ring wherein the two detectors are integrated, such as SPECT CT, PET CT, CT NMR and recently PET NMR.

These systems known in technology have the disadvantage of being very bulky and very expensive, so as to remain the exclusive prerogative of large industrial groups such as General Electric, Siemens, Philips and Toshiba, which can make products similar to each other, with minor differences.

In addition to the mentioned morphological imaging techniques, the use of ultrasound images for diagnosis is widespread in medicine; the main advantages of ultrasound techniques are represented by their ease of use without dosimetric requirements (in contrast to the scintigraphic ones, wherein it is necessary to use sources with X-rays) and by the excellent level of the obtainable images, usually obtained in a few seconds at resolutions lower than a millimeter, as well as with lowest cost per single application. In contrast, a disadvantage is represented by the fact that the detection of the images must be performed by very experienced staff, with obvious repercussions on the operating costs of existing equipments. Moreover, current ultrasound detectors have the further disadvantage of being not able to be integrated in a tomographic ring.

Among said ultrasound applications, in particular, the radio-guided intraoperative applications are here mentioned, which are based precisely on the use of ultrasound probes in oncological surgery, wherein experiencing a probe capable of working in echo-mode scintigraphic could be highly interesting.

In the prior art, in said field of cancer surgery, to date, to the knowledge of the Inventors, substantially one application solution comes out to be realized, which attempted to propose the use of ultrasound probes in dual imaging systems in medicine, but has the obvious disadvantages of being constructively very complex and, therefore, also very expensive.

It has been realized at the University of Berkley, Calif. USA, and proposes the realization of a detector echo-PET for imaging the prostate, where a complex and expensive system of laser pointers is used for sighting at each instant the position of the ultrasound probe and try to contextualize the scintigraphic image with the one coming from positron tomography (PET) [J S Huber et al., "Dual-Modality PET/Ultrasound Imaging of the Prostate", 2005 IEEE Nuclear Science Symposium Conference Record].

Recently a third solution has also been reported which involves the construction of a detector of ECHO SPECT type, i.e. provided with a pair of detectors, a first ultrasound one and a second scintigraphic one, which have however the disadvantage to be completely independent during the phase of echo-scintigraphic analysis and, therefore, require specific skills by the user of the detector.

Concerning the simultaneous detection of signals from gamma radiation and acoustic signals, US2012/032086 A1 describes a portable scanning probe for intraoperative use. The probe is an X-ray scanner integrated with a series of solid state photomultipliers. The device also comprises a location tracker able to acquire the position of the probe itself. While the probe is moved on the surface of the patient to be analyzed, the optical sensor acquires images of the field and a software superposes them onto the nuclear images to form a composite image. Although this probe has been proven with a ultrasound guide, the patent document does not specify the integration of the ultrasonic probe with the X-rays one, but only the use of two techniques per se as separated, the embedded images being by the way only the optical and nuclear ones.

US2009/030310 describes an endoscopic probe which contains in the head both a scintillator and an ultrasound sensor. However, it is specified (par. [0013]) that the scintillator is formed of a single crystal, and that this does not allow to realize a real three-dimensional tomography. This however is made by reconstruction using a traditional PET detector which is far from the probe.

A U.S. Pat. No. 4,995,396 describes an endoscopic probe which contains in the head both a scintillator and an ultrasound sensor. The two detectors are placed side by side or juxtaposed. The two devices collect the signals by an angular scanning, obtaining at the end an angular distribution of the count and echo signals. The imaging definition is linked to the plurality of simultaneous acquisition of a number of viewing angles whose selectivity in angle defines the spatial resolution of the system. It deals with an endoscopic probe in which the device has echo imaging functions, not of B-mode type, while the detector array has only a function of measuring the intensity of gamma radiation collected in a wide viewing angle and that does not offer any chance to process the signal intensity in order to make a spatial image of the radiation source. From FIGS. 3, 11, 35 and 40a can be deduced that the two detectors operating at 180 degrees and the collimator is used in order to limit the angle. In fact in 11, 35, 40a indicators of intensity of measured gamma radiation are shown and in no other figure neither the use of images gamma nor consequently fusions between images of two different modes are shown. The display of images is made so that the echo picture appears together with a bar graph of the intensity of gamma radiation. The gamma image is then not visualized, but a LED indicator divided into colored bars is used: the greater the number of illuminated indicator bars, the greater the intensity of the gamma radiation.

US2008/230705 A1 describes an endoscopic probe which contains in the head both a scintillator and an ultrasound sensor. However, the scanning direction of the two sensors is substantially orthogonal, and a tracking device for detecting the position of the probe is provided. Based on the data of the tracking device, the images of the scintillator are contextualized. Nothing is said however on the integration of ultrasound images.

U.S. Pat. No. 6,212,423 B1 describes an endoscopic probe which contains in the head both a scintillator and an ultrasound sensor. However, the scanning direction of the two sensors is not coincident, as specified in col. 7 I.22-27, and this poses problems in the superposition of the images obtained by the two sensors.

WO2004/042546 A1 describes an endoscopic probe which contains in the head both a scintillator and an ultrasound sensor. The endoscopic probe is provided with a tracking device for detecting the position of the probe. The direction of the two detectors is equal in the sense that the two detectors are placed side by side and are parallel, the field of view is not, however superimposed. Consequently, the system makes use of fiducial markers to align the images. Document WO2004/042546 A1 provides a protocol substantially rather than a device to optimize the comparison and the fusion of anatomical images with functional images, regardless of the techniques by which they are acquired.

EP 2347791 A1 describes an endoscopic probe which contains in the head both a scintillator and an ultrasound sensor. However, the scanning direction of the two sensors is not coincident, and this poses problems in the superposition of the images obtained by the two sensors.

Article of Pani et al. "Dual-Modality Ultrasound Detector SPET for Molecular Imaging", Nuclear Physics B. Proceedings Supplement, vol. 215, no. 1, 1 Jun. 2011, pp. 319-323, describes an integrated probe. The gamma counting rate in this probe is not beneficial and the recording of images is difficult.

SUMMARY OF THE INVENTION

The main object of the present invention is, therefore, to solve the disadvantages and problems still present in the prior art, realizing industrially, through a manufacturing process simple to implement and minimum realization cost, also for the typology of materials and devices to be used, a probe providing, with a single contact with the patient, an echo-scintigraphic integrated image of examined part of the body.

A further object of the present invention is to provide a practical and simple echo-scintigraphic probe, which is easy to use even by not highly specialized medical personnel.

A further object of the present invention, not less important than the previous one, is to provide a echo-scintigraphic probe shape such as to be portable, ie easily handled by medical personnel.

Further object of the present invention is a process of fusion of functional images obtained with the echo-scintigraphic probe according to the invention.

It is subject-matter of the present invention an echo-scintigraphic probe for medical applications, comprising:
an echographic probe comprising a plurality of piezoelectric bands extended along an axis y and adjacent to one another along an axis x perpendicular to said y axis, said y axis defining the scanning direction of the echographic probe;
a scintigraphic probe for the detection of gamma rays, comprising:
a collimator;
a scintillation crystal with a scintillation crystal section on a section plane parallel to the two directions x and y and perpendicular to an axis z;
said echo-scintigraphic probe being characterised in that the scintillation crystal, the collimator and the echographic probe are disposed in line, in the order along said z-axis, in such a way that they are integral with each other and such that:
the echographic probe constitutes an end of said echo-scintigraphic probe and is apt to contact, in use, a zone of biological tissue to be analysed;
the orthogonal projection of said echographic probe on said section plane overlaps said scintillation crystal section on a overlapping area smaller than or equal to the half of said scintillation crystal section.

The fact of the partial overlapping of the ultrasound probe to the scintillation crystal creates an area "in light" and an area "in shadow" compared to ultrasound and gamma rays. In this way, according to the method of the invention, the data detected by the scintillation crystal outside the orthogonal projection of the ultrasound probe can be compared with those obtained from the scintillation crystal within the orthogonal projection of the ultrasound probe. The latter portion of the scintillation crystal receives radiation obliquely also from the biological tissue area examined by the ultrasound probe, and thus can confirm or deny the presence of a body detected by the scintillation crystal below the ultrasound probe.

Preferably according to the invention, said collimator is a SLIT collimator with a plurality of collimation slits, and the piezoelectric bands of said plurality of piezoelectric bands are aligned to the collimation slits of said plurality of collimation slits.

Preferably according to the invention, said echographic probe is an echographic B-mode probe with quadrangular section perpendicular to said z-axis, the orthogonal projection of said quadrangular section onto said section plane overlapping said scintillation crystal section entirely along the direction x and partially along direction y for a portion not larger than its half.

Preferably according to the invention, said slit collimator presents slits with a length that is smaller than the dimension, in the direction of the same slits, of the scintillation crystal, the zone of the scintillation crystal outside the orthogonal projection of the collimator onto it being shielded with suitable absorbing materials, such as for example lead.

Preferably according to the invention, the probe further comprises, in line along said z-axis with the scintillation crystal and adjacent to it, a photo-detection system configured for the spatial sampling of the light distribution coming from the scintillation crystal.

Preferably according to the invention, said photo-detection system is a system with multiple detection elements, such as for example a multi-anodic PMT, or a system of small independent, semiconductor photo-detectors, for example of the SiPM type, assembled into an array.

Preferably according to the invention, the probe comprises, in line along said z-axis with the scintillation crystal and said photo-detection system, a detection and control electronics of the scintigraphic probe in a longitudinal portion of the echo-scintigraphic probe constituting a handle.

Preferably according to the invention, said collimator is provided in a head portion of said echo-scintigraphic probe, the echographic probe being positioned in such a way to protrude with respect to said head portion.

Preferably according to the invention, laterally to said head portion and laterally to the photo-detection system a plurality of lead plates for the shielding against radiations is provided.

Preferably according to the invention, the slit collimator presents slats having thickness equal to 20-30 hundredths of mm, oriented along the y-axis and evenly spaced by 1-2 millimetres along the x-axis by means of a rigid synthetic foam, optimizing as a consequence the obtaining of a perfectly linear scintigraphic image and, at the same time, maximising the efficiency of the echo-scintigraphic probe.

It is further subject-matter of the present invention a method for the functional integration of a pair of echographic and scintigraphic images contextually obtained by an echo-scintigraphic probe for medical applications, characterised in that said echo-scintigraphic probe is the probe according to the invention, and in that the following steps are executed:
P.1) acquiring the echographic image along a transversal plane defined by the x and z direction, and the scintigraphic image on a front plane parallel to the directions x and y, the directions x, y, z being defined in embodiments disclosed herein;
P.2) setting the resolution of the echographic image as equal to that of the scintigraphic image;
P.3) shifting the echographic image in such a way that its centre superposes to the centre of the scintigraphic image;
P.5) integrating the gamma counts of the scintillation crystal along the y direction, obtaining a final scintigraphic image constituted by a profile of counts along the x axis;
P.11) unifying the echographic image and said final scintigraphic image by superposing them.

Preferably according to the invention, between step P.3 and step P.11 the following further steps are executed instead of step P.5:
P.4) subdividing the scintigraphic image into at least three portions extending along the x-axis and consecutive along the y axis, wherein:
  a first portion overlapping the area of the orthogonal projection of the echographic probe onto said front plane;
  a second and at least a third portion;
P.5a) integrating the gamma counts of the scintillation crystal in said at least three portions along the y direction, obtaining corresponding at least three integrated counts profiles;
P.6) verifying the equality, along the x axis, of the counts integrated in step P.5a in said second portion and said at least a third portion, within a pre-defined error;
P.7) if the verification of step P.6 is negative, varying the area of said second portion and said at least a third portion in step P.4 and re-starting the integration of step P.5a;
P.8) if the verification of step P.6 is positive, comparing said at least three integrated counts profiles with each other;
P.9) if from the comparison of step P.8 it comes out that said at least three integrated counts profiles are qualitatively different from each other, varying the extension along y of at least two of said at least three portions, and re-starting from step P.4;
P.10) if from the comparison of step P.8 it comes out that said at least three integrated counts profiles are qualitatively equal to each other, choosing as final scintigraphic image one among said at least three integrated counts profiles or the sum of at least two of said at least three integrated counts profiles;
P.11) unifying the echographic image and the scintigraphic image by superposing them.

The portions B and C alone are not sufficient for the identification of structures of medical interest, since these portions could point at another area of the biological tissue to be analyzed. So, if they do not agree with the portion A, there is the need to reposition the probe.

Preferably according to the invention, said first portion coincides with the orthogonal projection of the echographic probe onto said front plane.

Preferably according to the invention, said integration of gamma counts of the scintillation crystal in said second and in said third portion in step P.5a occurs for each slit of the slit collimator in accordance with embodiments disclosed herein, and said verification of step P.6 occurs for corresponding slits.

Preferably according to the invention, if in step P.9 it is found that the profile relevant to the third portion differs from the corresponding profiles of the first portion and second portion, the profile of the third portion is utilized to subtract a background to said first portion and said second portion, and, instead of step P.10, the following step is executed: P.10a) choosing as final scintigraphic image one between the profile corresponding to the first portion or the second portion or the sum of the profile corresponding to the first portion and the profile corresponding to the second portion.

BRIEF DESCRIPTION OF THE DRAWINGS

The invention will be hereinafter described by way of illustration but not by way of limitation, with reference to the accompanying drawings, wherein:
FIG. 4a shows the echo-scintigraphic probe in use according to the invention;
FIG. 4b shows the paths of the gamma rays and the acoustic waves inside and outside the echo-scintigraphic probe of the invention, in longitudinal view.

FIGS. 11 to 16 show successive portions of a flow chart which illustrates by way of example the method of processing of the echo-scintigraphic images according to the invention;

FIG. 17 shows an example of an ultrasound image compared with the scintigraphic image, obtained by the method of the present invention;

FIG. 19 shows an example of an ultrasound image compared with three scintigraphic images corresponding to the three portions of scintigraphic probe indicated in FIG. 10, obtained by the method of the present invention;

DETAILED DESCRIPTION OF EMBODIMENTS

Figure 1:
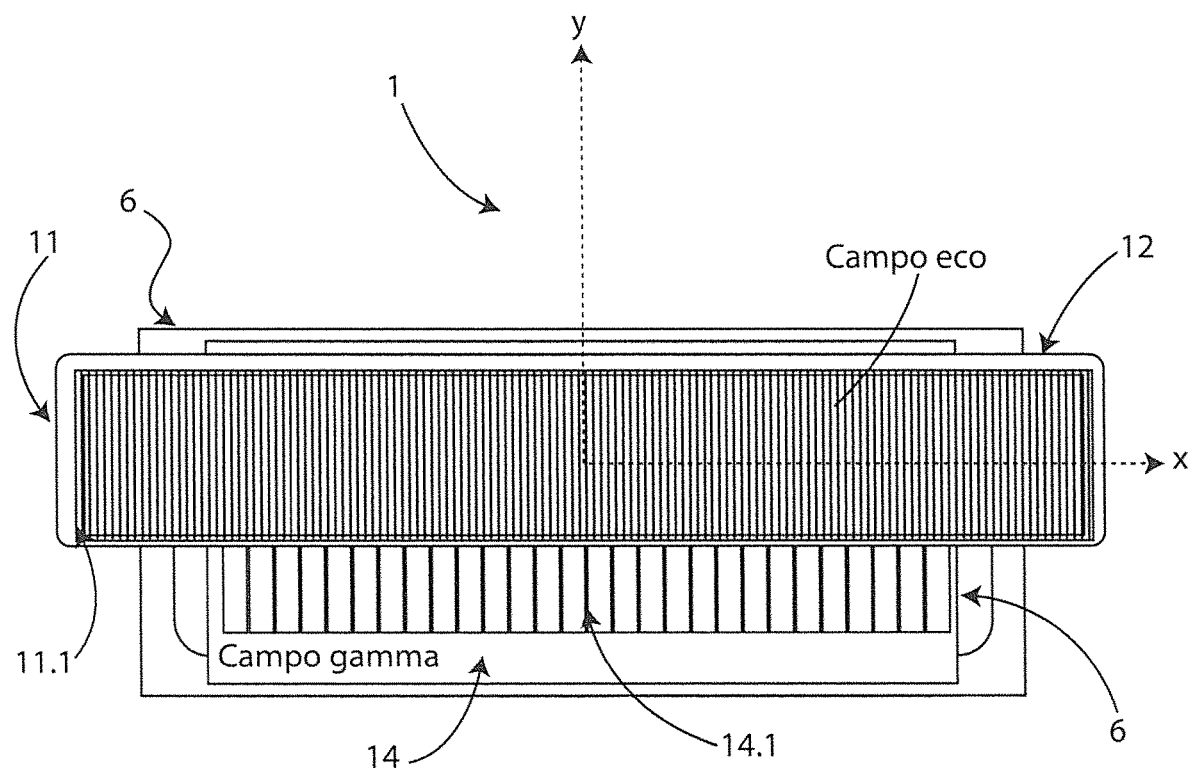
FIG. 1 is a schematic front view (x-y plane) of the echo-scintigraphic probe according to the invention.
Figure 2:
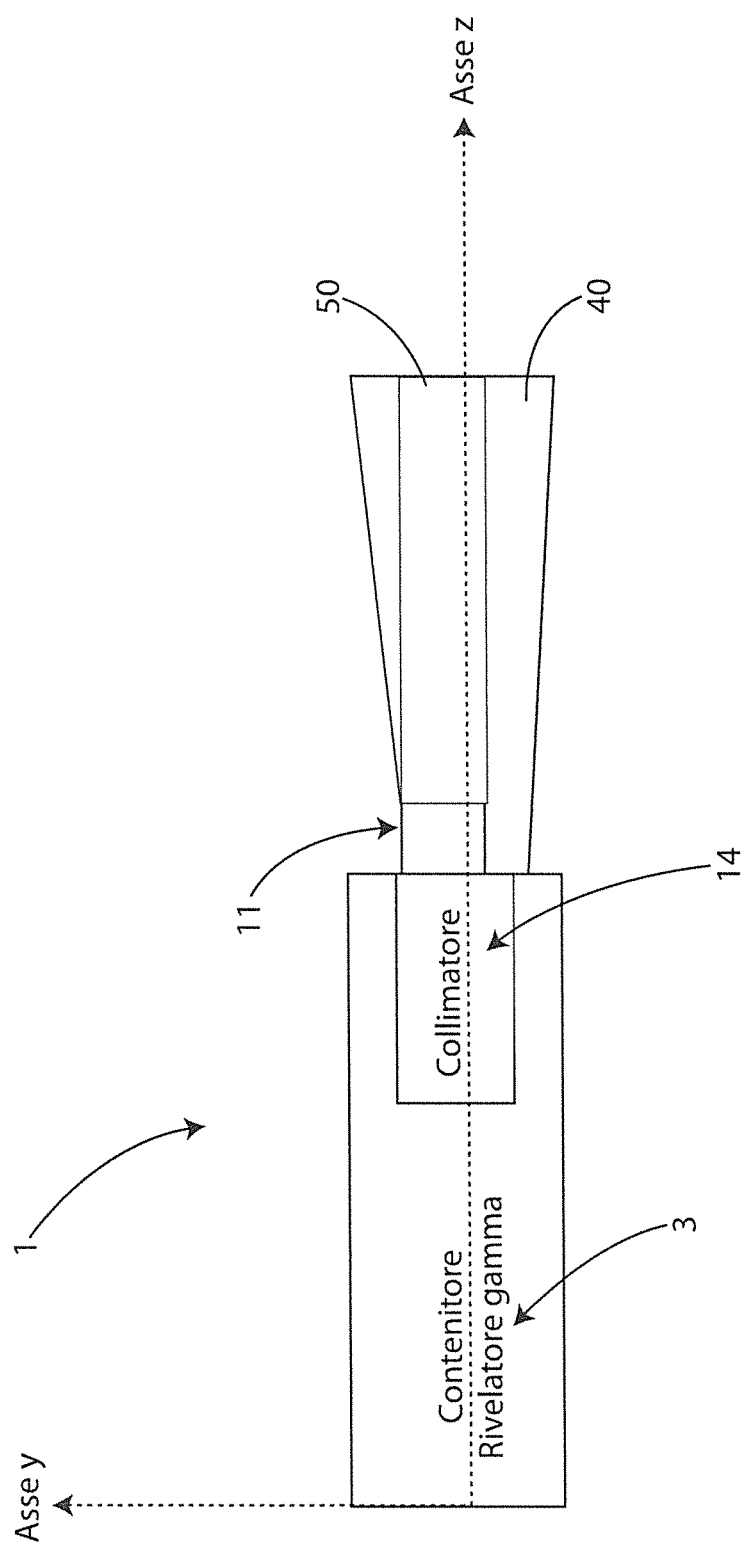
FIG. 2 is a schematic longitudinal (y-z plane) of the echo-scintigraphic probe according to the invention, with indication of the fields of activity for the ultrasound probe and for the scintigraphic one.
Figure 3:
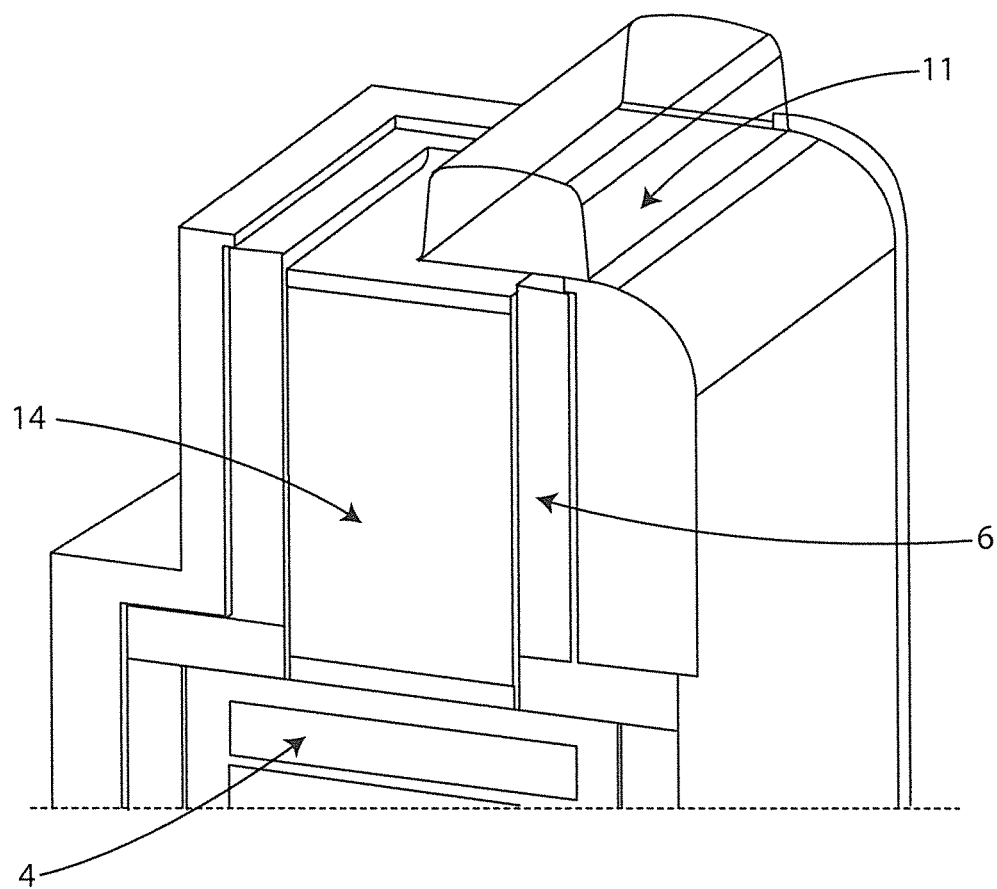
FIG. 3 shows a three-dimensional view of the head of the echo-scintigraphic probe according to the invention.

Referring to FIGS. 1 to 3, the echo-scintigraphic probe 1 according to the invention is schematically illustrated. The echo-scintigraphic probe is constituted by an echographic sensor and a scintigraphic sensor pointed in the same direction with the visual field of the second that contains the visual field of the first, which is mounted in such a way as to absorb a part of the gamma photons, producing a shadow on the plane of collection of the gamma photons of the scintigraphic sensor. More specifically, an echo-scintigraphic probe 1 is provided, which is placed in front of a collimator 14 which in turn is placed in line with a gamma camera 3. As can be seen from FIG. 2, the ultrasound probe 11 covers only a part of the collimator 14 and is slightly shifted from the axis of the collimator ("asymmetric" mounting). Despite this, the field of action 50 of the ultrasound probe and that 40 of the scintigraphic probe are in the Z direction, meaning that the scintigraphic probe sees the overlapping of planes produced along the Z-axis while the ultrasound probe sees in depth along the Z-axis.

The collimator 14 is a slit collimator laterally shielded with a lead shield 6 (a plurality of screens), which extends to the entire gamma camera 3. The echo-scintigraphic probe 1 provides, in a preferred but not limiting solution, the use of a linear probe with 192 piezoelectric crystals (strips) 11.1, with the size of sixty millimeters×twelve millimeters, with a total thickness comprised between five and eight millimeters including the support of the crystals.

A scintillation crystal 4 is close to the collimator 14, and is preferably constituted by a compound of sodium iodide (NaI) and doped Thallium (Tl). It defines the level of detection of the echo-scintigraphic probe.

Figure 10:
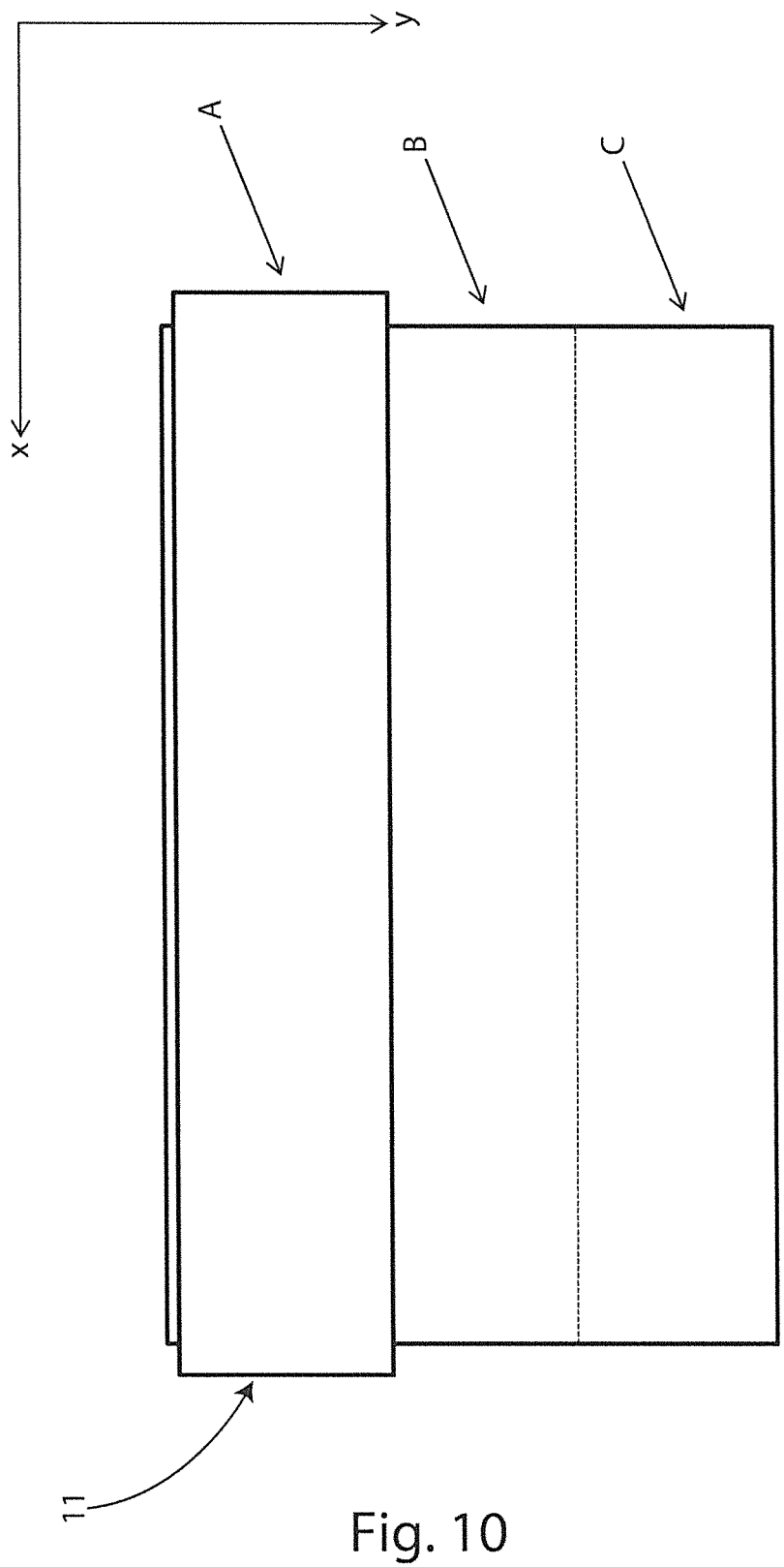
FIG. 10 shows a subdivision of the front field of the scintigraphic probe, in the device according to the invention.
Figure 11:
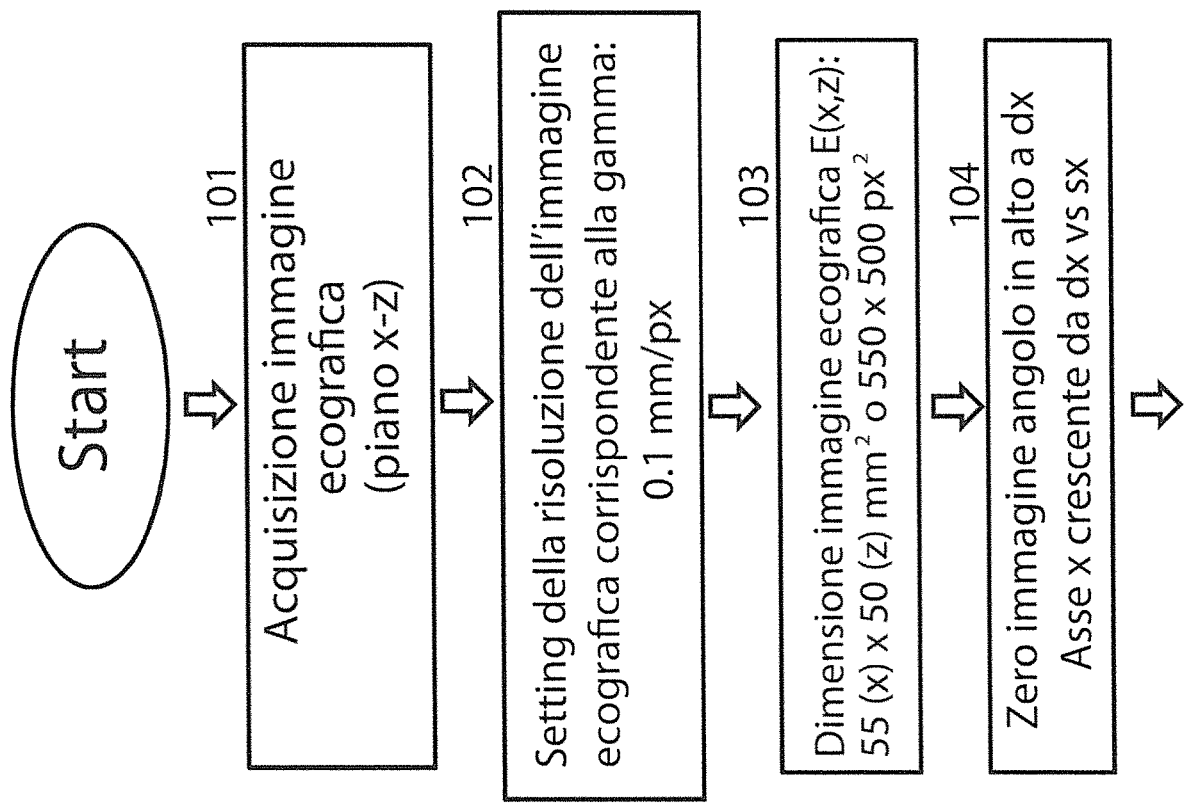
Figure 12:
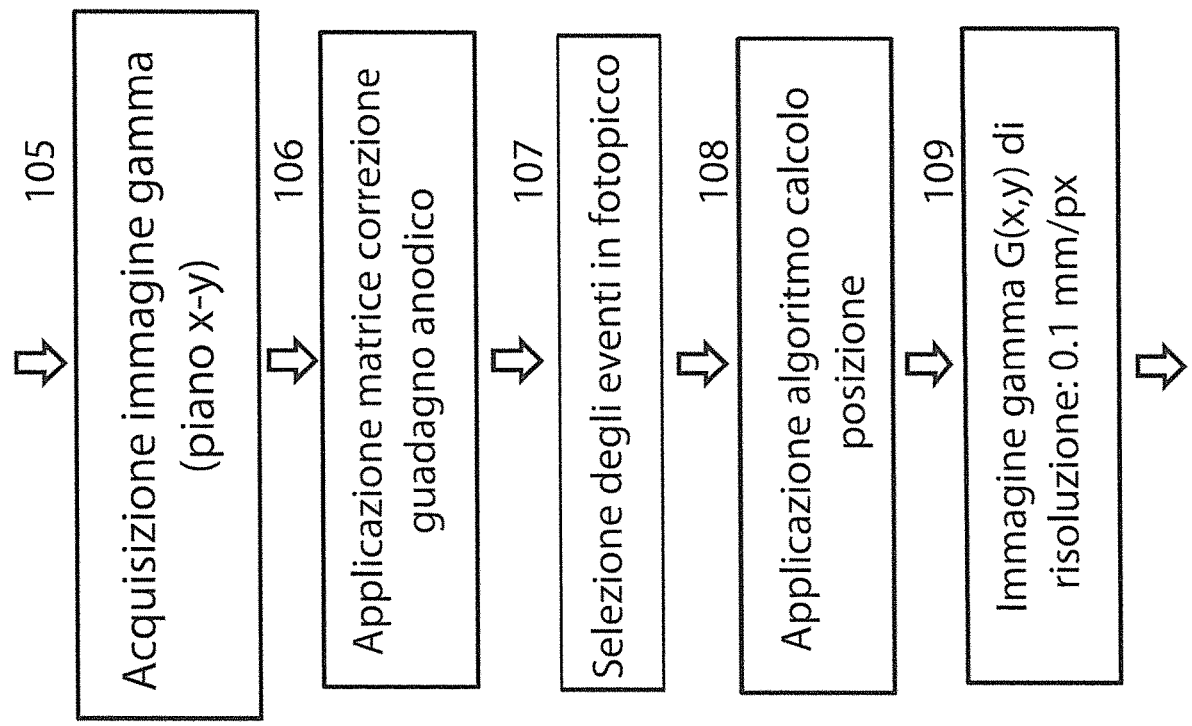
Figure 14:
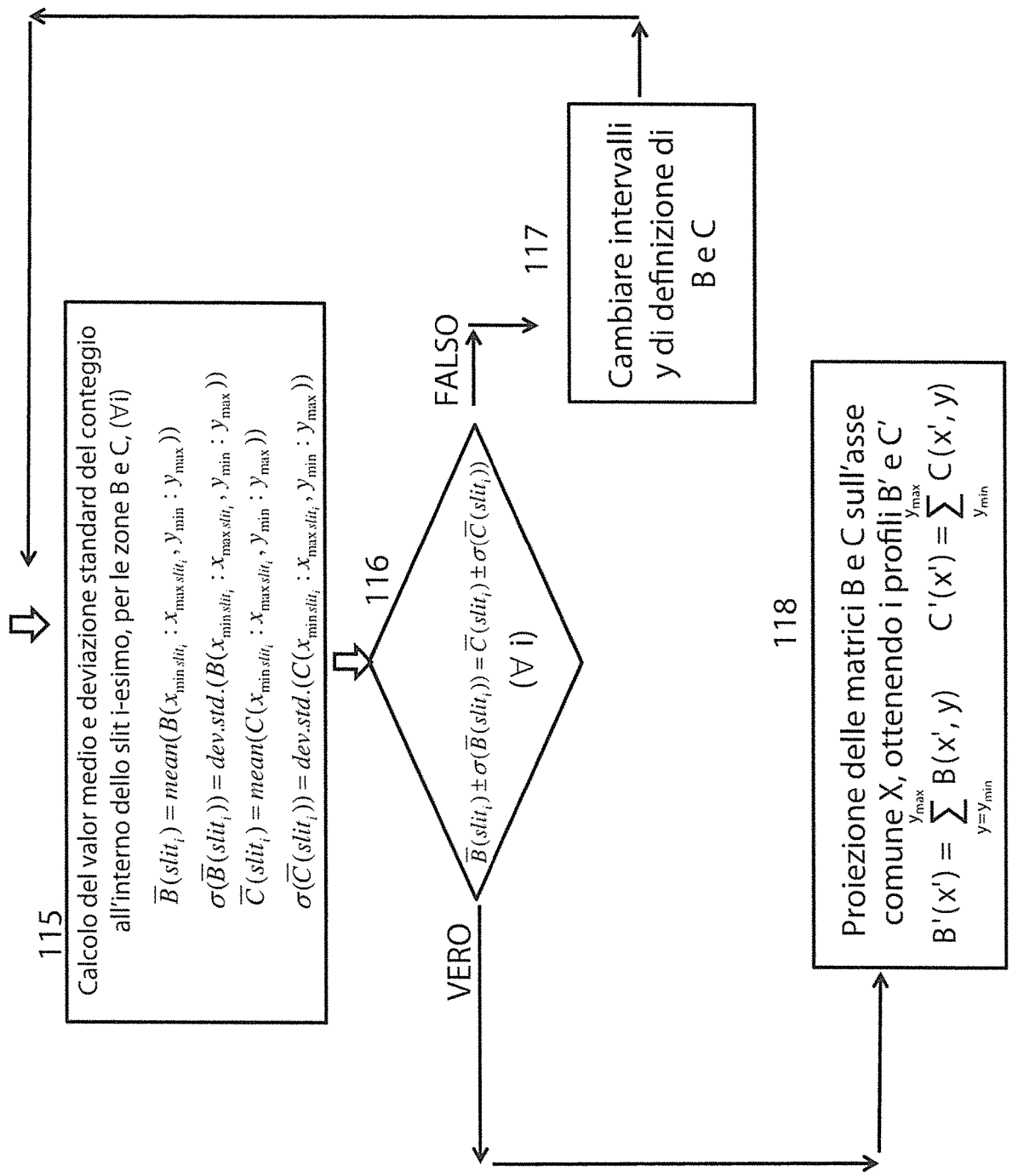
Figure 15:
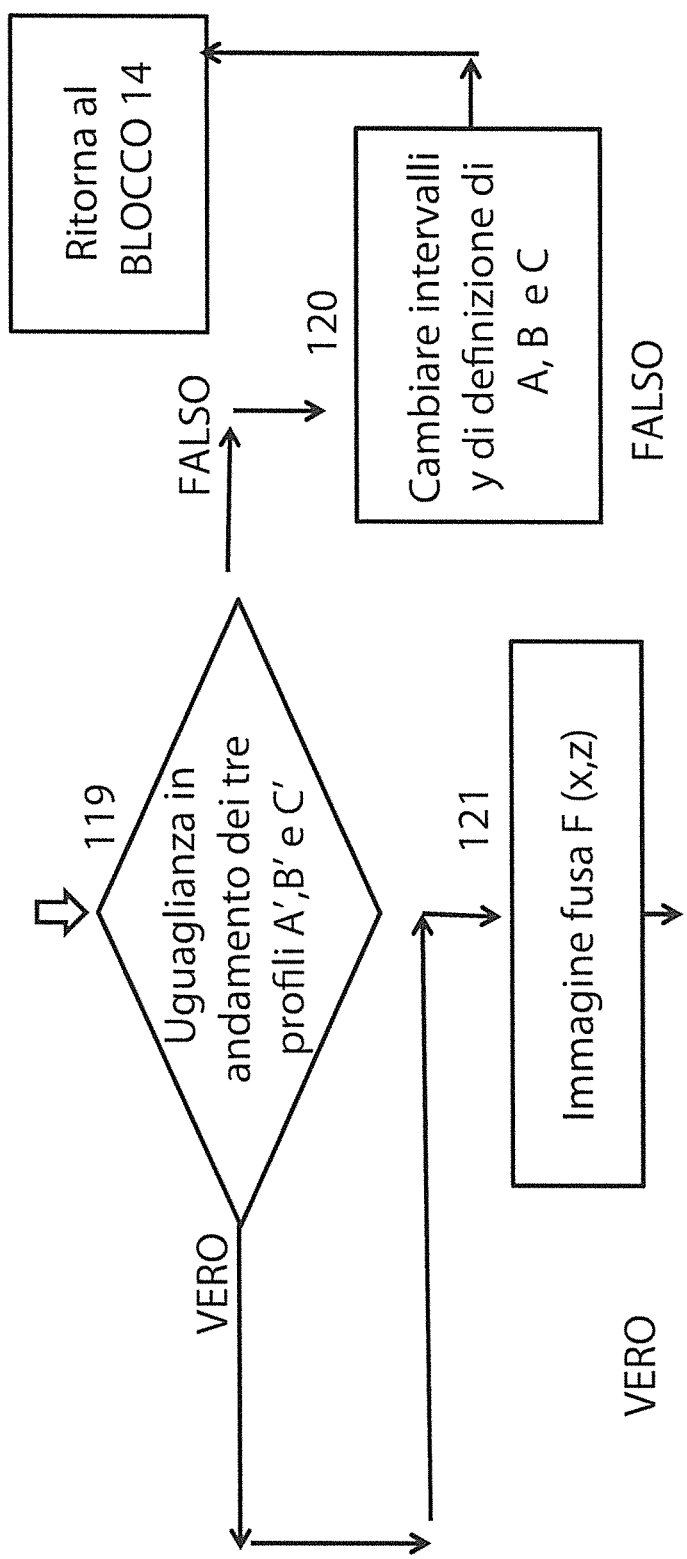
Figure 16:
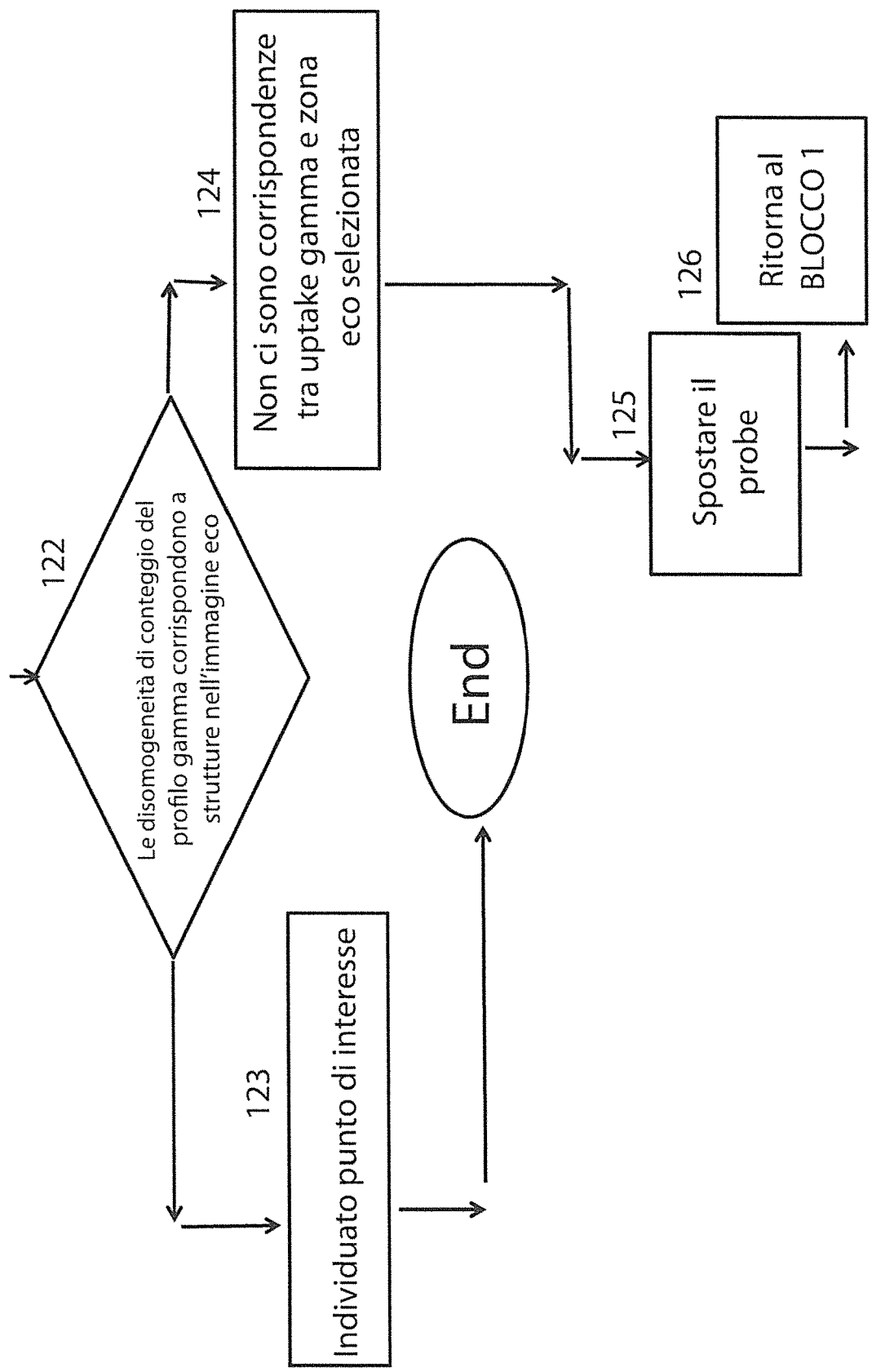

As may already be seen from these figures, the ultrasound probe 11 is positioned above the plane of the collimator 14 and retained therein with one protruding end 12 in order to facilitate the direct contact with the part 20 of the body of the patient 13 to be examined (see. FIG. 10). In one embodiment, the size of the ultrasound probe along the x-axis is greater than that corresponding of the slit collimator, and allows having a greater view in the phase of centering.

FIG. 4a shows the use of the probe 1 according to the invention with a patient 200.

FIG. 4b shows the path of the gamma rays and the acoustic waves inside and outside the device according to the invention in contact with the patient 200 of FIG. 4a. A formation 210 of interest (e.g. neoplasia) in the patient 200 emits gamma rays and reflects ultrasound generated by the ultrasound probe which is part of the probe according to the invention. Along the X axis, there is a total overlap of the active areas of the two detectors (ultrasound and scintigraphic), which does not prevent the same detectors to operate correctly. The image on the right shows the echographic detection (ovoid formation) and gamma counts overlapped by the method of the invention, illustrated in the following.

Figure 5:
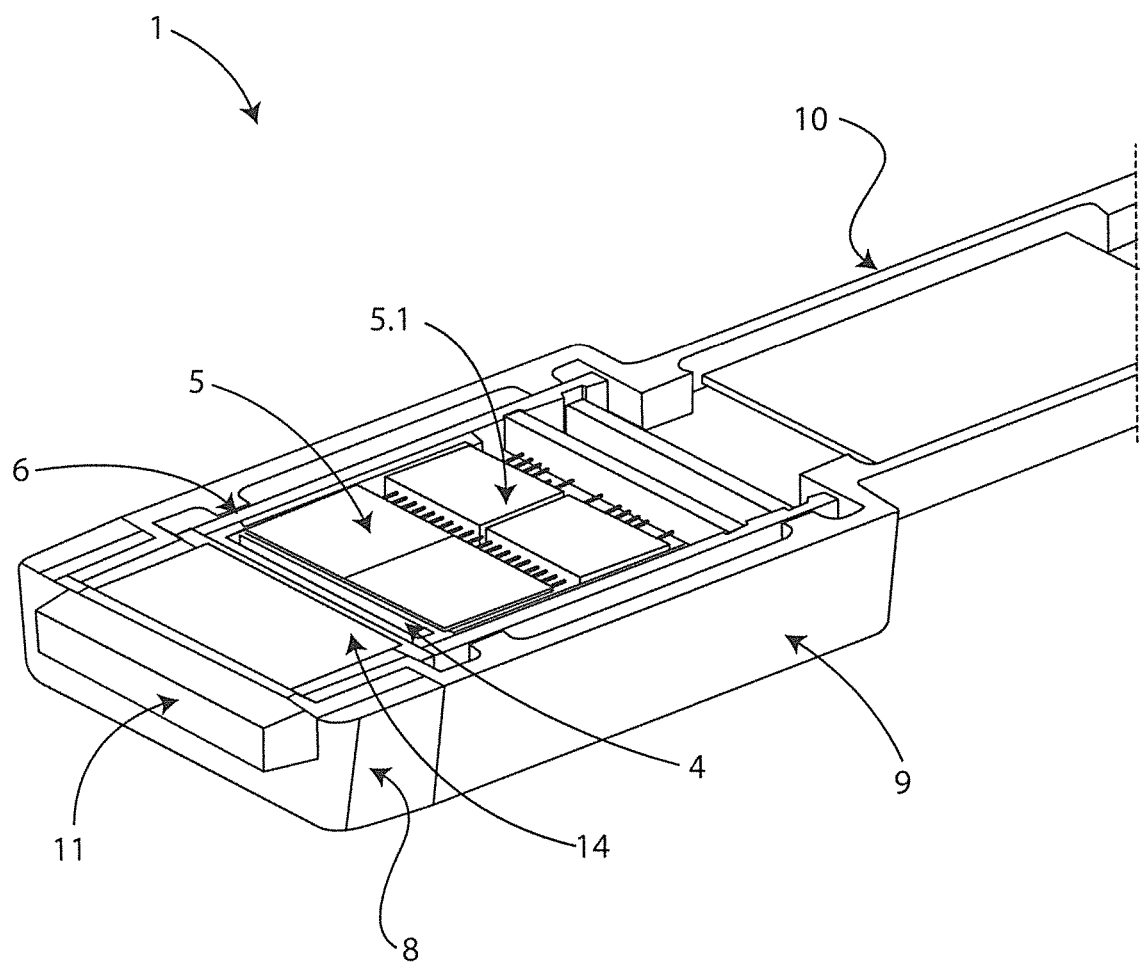
FIG. 5 shows a perspective view of a cross-section of the head of the echo-scintigraphic probe according to the invention.

FIG. 5 shows the same arrangement of the previous figures, in which however both the photomultipliers 5 behind the scintillation crystal 4, and the dividers 5.1 in turn behind the photomultiplier 5 are shown. The figure shows the subdivision of the probe in a head 8, a body 9 and a handle 10. The dividers have the function of distributing in a progressive way the voltage at the dynodes of the photomultiplier. The dynodes are the devices responsible for the propagation of the electrons inside the photomultipliers for the purpose of amplifying the original signal from the photocathode, but other devices multipliers can be advantageously used as well.

Figure 6:
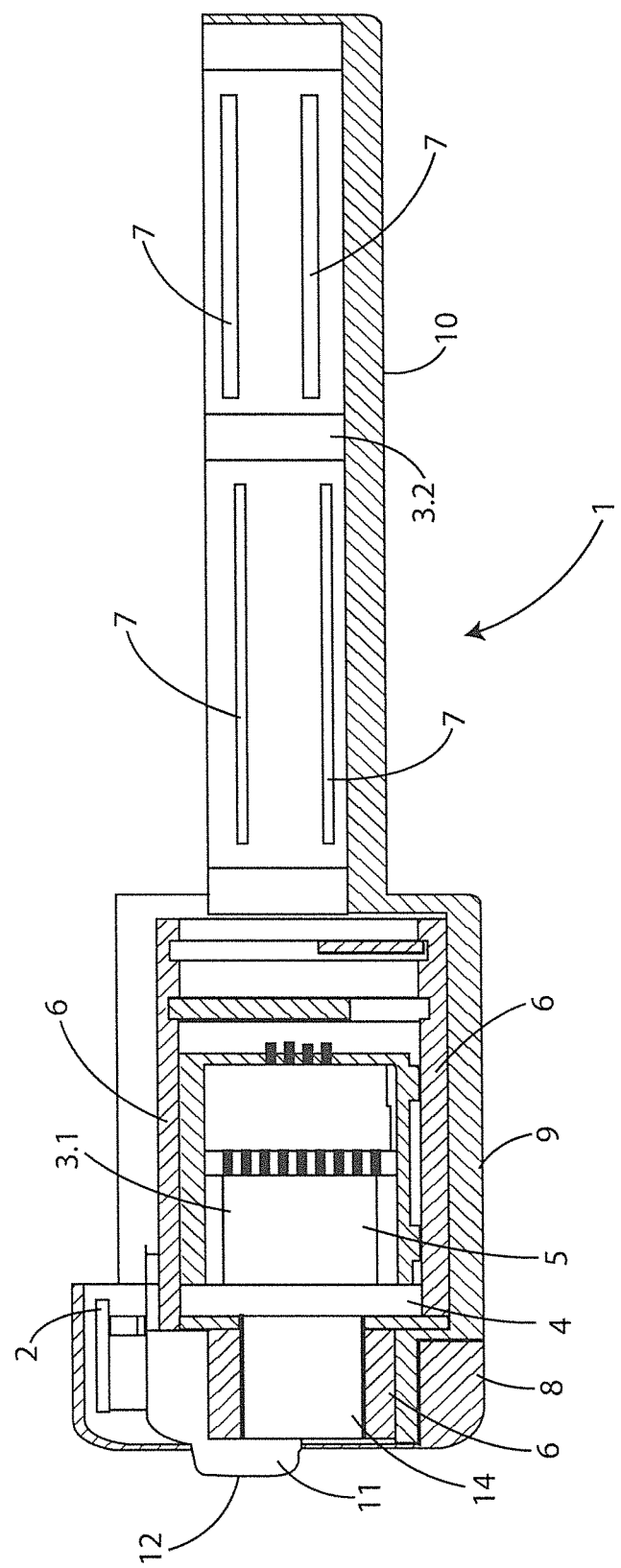
FIG. 6 shows a longitudinal section of the echo-scintigraphic probe according to the invention.
Figure 7:
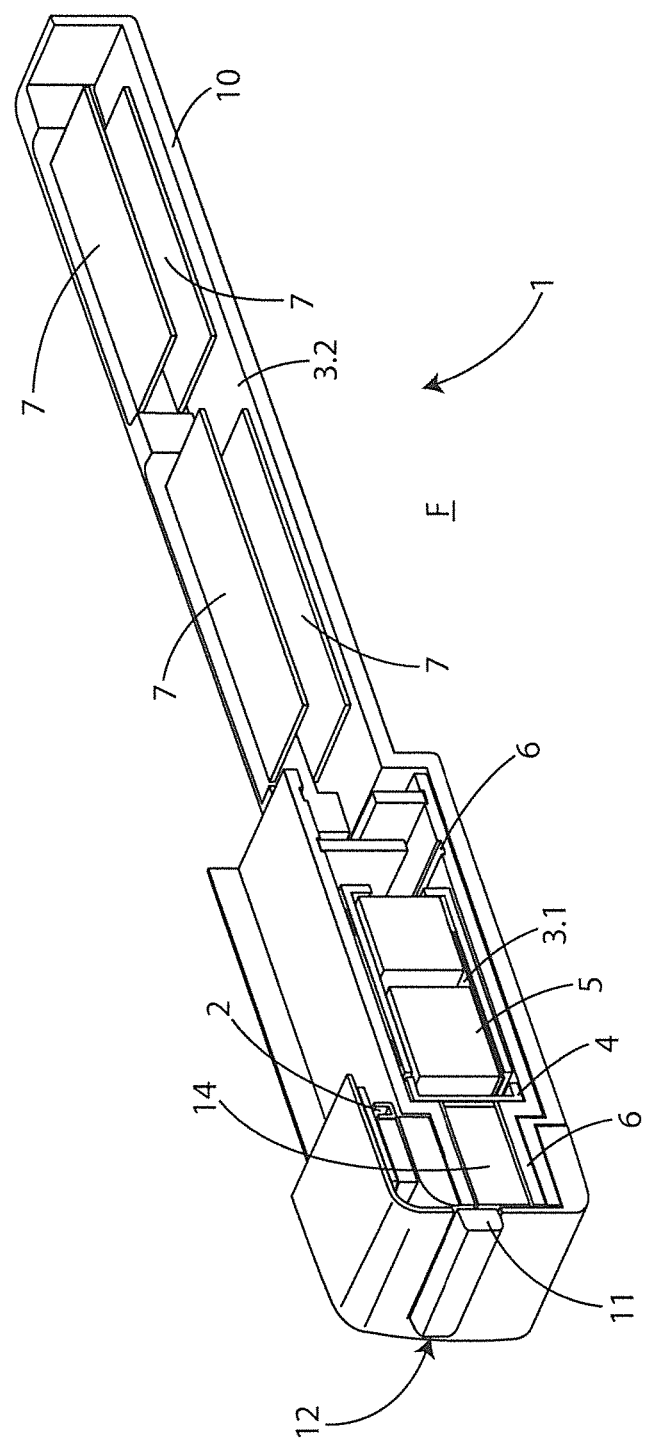
FIG. 7 shows a perspective view of the echo-scintigraphic probe according to the invention, open.
Figure 8:
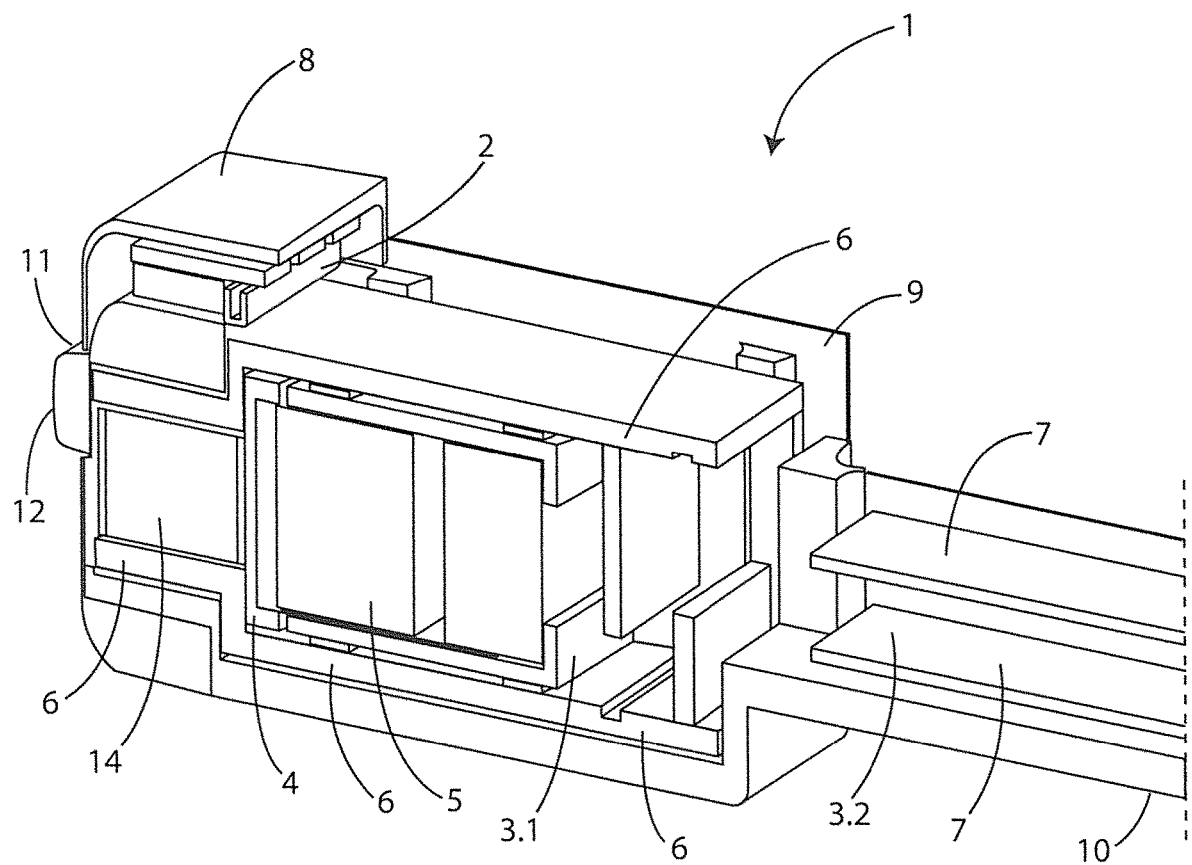
FIG. 8 shows in greater detail the head in FIG. 7.

FIGS. 6-8 show in greater detail the section of the entire probe. In addition to the already specified elements, readout electronics 7 of the gamma camera 3 is shown which is housed in the handle 10 of the probe, the I/O cables 2 for the transmission of echographic signals, and the division between one part 3.2 of the gamma camera housed in the handle (readout electronics being considered part of the gamma camera), and the sensitive part 3.1 placed immediately behind the head 8.

Figure 9:
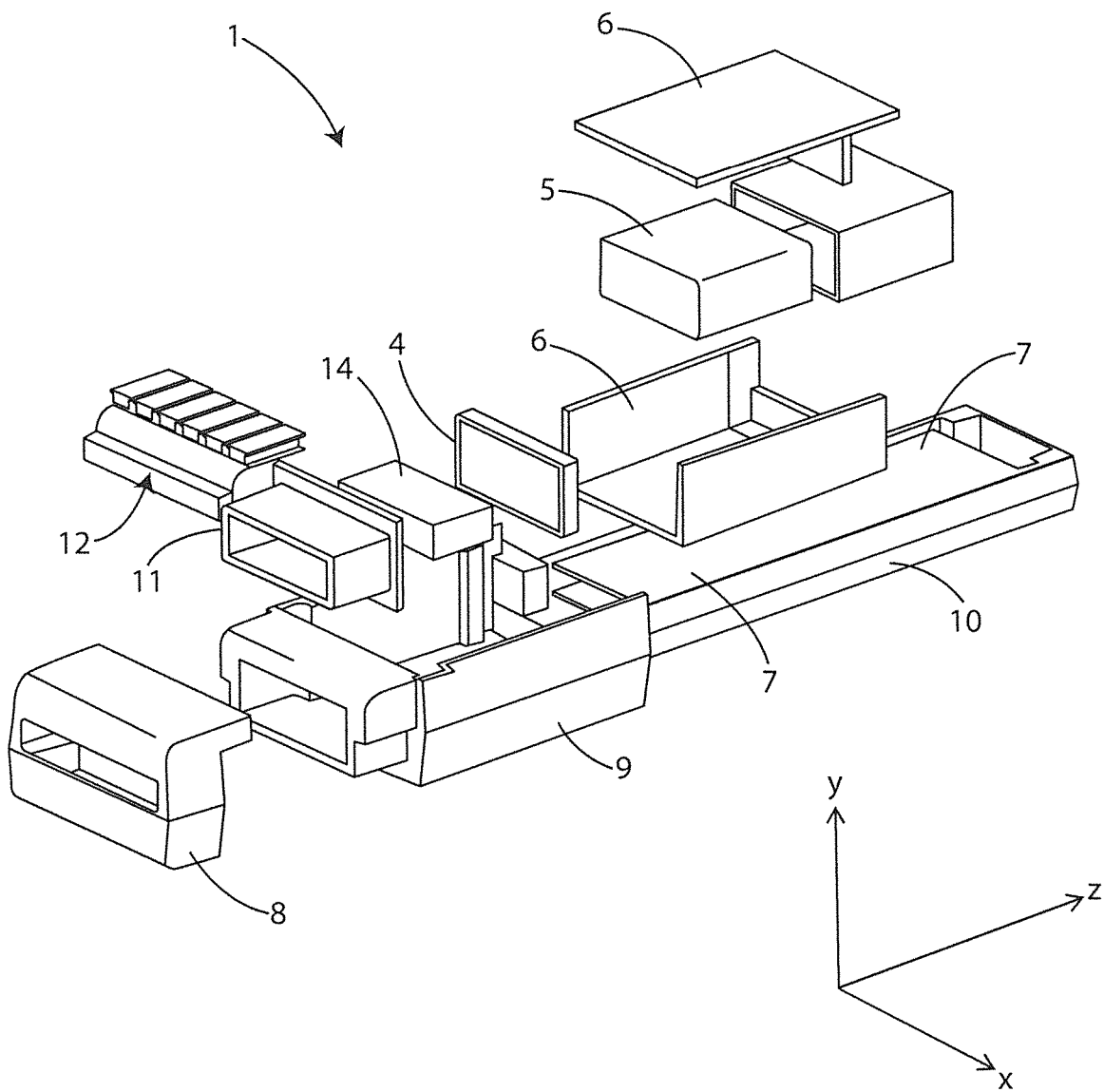
FIG. 9 shows an exploded view of the echo-scintigraphic probe according to the invention.

FIG. 9 shows an exploded view of the echo-scintigraphic probe 1 according to the invention, with the indication of the elements described above.

In the following further constructional details of the probe are provided which has been just described in its components.

The echo-scintigraphic probe 1 provides, in a preferred, but not limiting, solution the use of an ultrasound linear probe with 192 piezoelectric crystals, with dimensions of more than sixty millimeters×twelve millimeters, with a total thickness of between five and eight mm including support of the crystals. The ultrasound probe consists of linear strips of sensors of length less than 12 mm and a width between 0.2 and 0.4 mm.

In order to minimize the total thickness of the walls of the echo-scintigraphic probe 1 and the overall dimensions of the system constituted by the union of the ultrasound 11 and scintigraphic 3 probes, connectorization has been designed with flexible cables such to allow positioning of the ultrasound probe 11 on the collimator plane, allowing connectors to be able to develop on the lateral plane of the detector.

The ultrasound probe can optionally be immersed in an oil bath via a flexible envelope to improve the quality of ultrasound images.

The I/O (Input/Output) data transmission cable 2 interfaces with dedicated connectors of "clip-clap" type on the side wall of the box of the gamma camera 3.

The absorption measurement shows that with the asymmetrical installation according to the invention (of the ultrasound probe with respect to the scintigraphic probe, see above) the photon flux incident on the scintillator in the overlap region is reduced up to a maximum of 40-30%. Said reduced absorption is primarily due to the thickness of the absorber material for supporting the piezoelectric crystals 4. This attenuation, however, is considered a good compromise compared to current technological performance of known scintigraphic probes and does not limit the performance of the echo-scintigraphic device. Moreover, as will be described in detail hereinafter, the ability of validating the quality of the signal collected by the scintiscanner is provided.

The detector or gamma camera 3 is composed of two position-sensitive photomultipliers 5, of the type Hamamatsu R8900-00-M16 of about a square inch of area (it is recalled that one inch equals approximately 25.40 mm, and then a square inch is equivalent to 25,40×25,40 square millimeters). Each photomultiplier comprises metal channel dynodes and a 4×4 anode matrix.

The two photomultipliers are coupled to a continuous crystal of NaI:Tl 4 with size of 51×26 square mm and four millimeters thickness. Said crystals of NaI:Tl 4 have usually good if not excellent spectroscopic performance, together with an economical price, an high efficiency in luminescence, with a very low, if not negligible, self-absorption of the scintillation light.

The system is finally equipped with a lead collimator 14 provided with slats of the "SLIT" type, very valuable for the formation of a one-dimensional profile of the scintigraphic image.

The gamma camera 3 is able to obtain images of the bio-distribution of a radio tracer for frontally incident radiation, while maintaining a field of view 40 broader than that 50 of the ultrasound probe 11 (see FIG. 2). The radiation impinging laterally is shielded with thin sheets of lead 6, limited to the crystal 4 and the photomultiplier 5, so as to reduce the weight of the entire system consisting of the echo-scintigraphic probe 1.

The slats of the collimator have a thickness of 25 hundredths of a millimeter, oriented along the minor axis (axis along which the spatial resolution does not occur) and equally spaced of 1.5 millimeters along the main axis by means of a rigid synthetic foam.

The choice of the size of the collimator (50 mm) was carried out in order to optimize the obtaining of a perfectly linear scintigraphic image and at the same time, maximize the efficiency of the echo-scintigraphic probe 1, forming a scintigraphic image in a few seconds.

Collinearity of ultrasound probe and scintigraphic probe is established by the alignment of the piezoelectric strip with the interspaces defined by the slit collimator, while the detection plane is defined by the scintillation crystal.

The interspaces between the walls of the slit are aligned to one or more strips of piezoelectric sensors. In a prototype, the septa of the collimator have a size between 0.1 and 0.5 mm. The degree of collinearity is defined by the focusing degree of the ultrasonic beam and the gamma rays minimum acceptance angle determined within a maximum of 4 degrees, typically +/−2 degrees at the center of the width of the collimation slit.

The linearity in position is guaranteed to have an average sensitivity (defined as $\sigma/N$ ½ wherein $\sigma$ is the spatial resolution and N is the number of collected events) for a number of gamma rays detected within the slit collimation having value smaller than +/−0.1 mm and anyway not greater than +/−0.4 mm for a single interaction of a gamma ray. This ensures in the central and longitudinal slot collinearity within an error of less than +/−2 degrees.

The detector array operates with two angular intervals of acceptance of gamma radiation: one parallel to the collimation slit (+/−20 degrees) and a very selective one perpendicular to the slits (+/−2 degrees).

This angular condition has a high resolution along profiles perpendicular to the slits, the wide angular range along the slit produces images related to the source placed in the field of view of the ultrasound probe, but also images generated by gamma radiation coming from other areas.

The wide acceptance angle along the collimation slit allows to detect the presence of sources outside the field of view in the case of strong counting gradients revealed inside the slit. The precise localization of the source along the axis orthogonal to the slits allows to calculate the origin direction of the radiation produced by the source external to the field of view.

The spatial resolution of the scintigraphic detection system can be better than 1 mm FWHM, to allow the identification on images of the slit collimator septa in parallel bundles gamma irradiation conditions. This identification of the septa is the basis of the definition of the reference system in the definition of collinearity of the echo-gamma images, together with the alignment of the two detectors.

The verification of the longitudinal alignment of the ultrasound probe with respect to the scintigraphic detector is performed through irradiation of the detection system integrated with parallel beams of gamma rays (obtainable for example by a distant source). From the profiles of the absorption gamma image, which have been obtained in a direction parallel to the slits of the collimator, distributions are obtained, which are similar to Gaussian, whose average values will define a line corresponding to the longitudinal axis of the ultrasound probe and define its alignment orthogonally to the collimation slits. The Gaussian profile of the absorption caused by the ultrasound absorber mounted on the rearside of the ultrasound probe has a FWHM amplitude comparable with the width of the echo probe and is related to the deviation from parallelism of the gamma rays and to the spatial resolution.

To ensure the best spatial linearity of the scintigraphic detection system, the collimation system will have a width (length of the slits) smaller than the area of detection of the actual scintillation crystal that will be screened with suitable absorbers materials 6 such as Pb. The presence of events in the screened area will be considered as the amount of gamma rays incident on the detector with an angle larger than that of acceptance defined by the collimation slit.

The readout electronics 7 is of the multi-channel type (in the preferred but not limiting solution, a reading electronics with 16-channel per photodetector, i.e. with 32 independent channels has been chosen) so as to be able to record the distribution of light for each single scintillation. In this way, it is possible to intervene on the individual distributions of light event by event, making instantly the relative necessary corrections. For example, usually these corrections are due to the incidence angle of the photons (depth of interaction—DoI) and the distortions of "PSF" of light due to reflections that occur within the crystal.

The reading of the 32 channels provides a second unique advantage of the invention, that is, it makes it possible to decide whether or not to use the two-dimensional image array or, alternatively, to promote larger counting rate (up to a double value) and record only the mono-dimensional image, allowing to work only on 16 channels, to have the single image profile in the projection that takes place parallel to the main axis of the gamma detector 3.

The ultrasound detector 11 allows, also, to obtain morphological images without the limitations due to the use of ionizing radiation (DOSE) as is the case for systems that employ "X" radiation, for example CT SPECT or CT PET.

The probe according to the invention has been, in fact, also designed to obtain images in a short time: a few seconds for the ultrasound image (even less than three seconds) and five to fifteen seconds for the scintigraphic image, compatibly with the typical acquisition rates of ultrasound images in the current diagnostic practice. The novelty of such performances is just inherent to the choice of a scintigraphic detector that is equipped with a very high efficiency "SLIT" collimator, about ten times the average characteristics of scintigraphic systems of equivalent applications.

In principle, for the foregoing, the ultrasound examination can be repeated several times and in a short time. In addition, the scintigraphic probe 3 can, through the image of the ultrasound probe 11, optimize its diagnostic capabilities with correct location of the lesion of the object to be seen. The ultrasound image is used both in the initial phase of localization, and in the final phase, subsequently to the scintigraphic acquisition, to confirm that the vision volume was correct.

Referring to FIGS. 6 to 9, in order to reduce the weight of the same container constituting the body 9, the head 8 and the tail 10 of the echo-scintigraphic probe 1, the container has been realized with the technique of synthetic polymers three-dimensional printing, with a plastic material (nylon and aluminum) that guarantees excellent resistance already with thicknesses between one and two millimeters only.

Optionally, to improve the ergonomics of transport of the echo-scintigraphic probe one can predict the further installation of a pair of handles that facilitate the use of the same echo-scintigraphic probe 1, given that the same appears slightly unbalanced forward, that is, towards the ultrasound "probe" because of the presence of the lead screen, which is present only in the frontal area of the radiation detector array 3.

The industrial manufacture of the echo-scintigraphic probes 1 of the present invention is simple and starts from the realization of the molds of the head 8, the body 9 and tail 10 of the plastic housing of the probe 1. These elements 8-9-10 constituting the casing of the probe 1, subsequently assembled together, have been designed to optimize the occupied space and the relative placement in them of the previously mentioned components.

A Method of Acquiring and Processing the Images

In relation to FIGS. 10 to 16, it is now described an embodiment of the procedure of acquiring and processing images, which is able to exploit the peculiarities of the integrated probe described above.

FIG. 10 shows three zones in which the field of view of the scintigraphic probe is divided. There is a zone A which is the one on which the ultrasound probe is superimposed, an area B located just beneath of this, and a third zone C located just below the latter. The three zones A, B, C are thus contiguous and constitute a division of the field of view of the scintigraphic probe. Clearly, the three zones A, B, C can also be of different sizes, the first area A being however always at least superimposed on the field of action of the ultrasound probe, or equal to the field of action of the ultrasound probe. Furthermore, the method according to the invention may also provide more than three zones, although in the present description reference will be made only to three zones.

The method starts with the acquisition of the ultrasound image (block 101) on the x-z plane of the previous figures. The contribution in the y direction is integrated as a projection on the x, z plane.

Within the acquisition phase of the ultrasound image, the resolution of the ultrasound image is set (block 102), and then that of the gamma image so as to make them equal (number of mm per pixel). In a prototype, the ultrasound device has 4 default setting. Typically a setting rather than another is defined depending on the size of the examined area, the size and depth of the object under examination. This procedure does not affect anything in the following, because the ultrasound device provides a reference dimension through a kind of ruler.

The physical dimension of the ultrasound image is determined (block 103) on the basis of the correspondence carried out in block 102.

The zero image (104) is then set: the position corresponding to zero of the Cartesian axes in the image, for example in the vertex at the top right, with axis increasing from right to left.

Subsequently (block 105) the gamma image is captured in the x-y plane. Block 105 includes blocks 106-111 as substeps to achieve the scintigraphic image definition.

At this point (106), a suitable matrix is applied on the sampled signal (from the anodes of the scintillator) of the scintillation light, to the end of standardizing the gains of the individual anodes. This in order to make homogeneous the information of the individual anodes that arrive from the factory with different gains. The procedure is similar to that known in the field of detectors for nuclear medicine.

Subsequently (block 107), the histogram of the distribution of the amplitudes of the signals coming from the scintillator is constructed. The full energy peak, i.e. the portion of the spectrum corresponding to events whose released energy corresponds to that of the incident photon, is determined. The selection of events in full energy peak, i.e. the selection of all events where the released energy is contained in the full energy peak spectrum, is carried out. This only affects the scintigraphy and is a process known in nuclear medicine.

Subsequently (block 108), an algorithm is usually applied in the prior art, which is necessary for the identification of the interaction point of the photon on the scintillation crystal (starting from the anodic detection, the point of interaction with the crystal that is facing is reconstructed).

Still, (block 109), the gamma image G(x,y), which is a two-dimensional image obtained by the detector array in the x, y plane, is constructed. The contribution in the z direction is integrated as a projection on the x, y plane. The only common direction between the echo E(x,y) and gamma G(x,y) matrices is the x direction.

The image resolution (applying both for the echo image and the gamma image) is measured in number of image pixels within a mm (see above).

The size of the image (block 110, it applies to both the ultrasound image and the gamma image) is determined, as the physical dimension of the image (in pixels or mm) corresponding to the actual size of the object shown in the image itself.

The zero of the image (block 110) is then set: zero position corresponding to the zero of Cartesian axes in the image.

In the subsequent step (block 112), since the length in mm of the ultrasound image along the x direction, is different from that of the gamma image along the same direction, it is necessary to shift along this direction the gamma image, so as to match the image centers in this direction. The shift procedure is defined using the procedure x'=x−a.

Subsequently (block 113), the gamma image is divided into three zones along the y direction. A zone is in the field echo probe (A) and 2 are outside the field of echo probe (B and C). The limits in y of the three zones are: for A (0: n), for the B area (n+1: m) and for the C area (m+1: 261), wherein n and m are numbers of pixels and 262 is the pixel size along the y axis.

In the subsequent step (block 114), from the A area determined in block 113, the image profile is obtained, which is understood as the sum of image counts in the y direction. This profile is similar to a vector, in the direction x', termed A'.

Subsequently (block 115), the mean value and the standard deviation of the gamma counts are calculated for each of the slit of the collimator in the image areas B and C.

Subsequently (block 116), it is verified that the average value of counting between the same slits of the two zones B and C (along the y axis) is the same within the error defined by the standard deviation.

In the subsequent step (block 117), if the condition of equality of the block 116 is false, then the intervals in y defining the zones B and C are re-defined.

Subsequently (block 118), if the condition of equality of the block 116 is true, one continues obtaining, as for the area A in block 114, the image profiles of the B and C zones by summing the counts along the y direction.

Subsequently (block 119), a verification is performed as to whether the trends of the three profiles A', B', C' are equal.

Subsequently (block 120), if the condition of the block 19 is false, the process returns to block 113 for the redefinition of the three sub-images (areas) A, B and C.

In the subsequent step (block 21), the ultrasound image (E (x, z)) merges (overlapping) with the one-dimensional image obtained by either the best gamma profile among A', B', C', or from a sum of the profiles A', B' and C' (or only two of them), obtaining an image F(x, z).

Below (block 122), it occurs that the non-uniformity of count (maximum) in the gamma profile correspond to a structure in the image ultrasound.

In the next step (block 123), if the condition of block 122 is true, then the area of interest has been determined.

Subsequently (block 124), if the condition of the block 122 is false, it means that there is a correspondence between the gamma emission and identified ultrasound structures and so it is needed to look for another structure to be analyzed by moving the probe. This is an important point, because the medical analysis can be driven by both the ultrasound probe and the scintigraphic probe, as the correct event is determined by the coincidence of the two pieces of information.

In the next step (block 125), you move the probe to another area of interest. Finally (block 126), the procedure is repeated from block 101 without image calibrations, already made.

The result of this procedure is shown in FIGS. 17 to 20.

In particular, FIG. 17 shows an example of the above three images A, B, C compared separately with the ultrasound image. In all three profiles of the gamma image the contribution of the lesion is identifiable.

Figure 18:
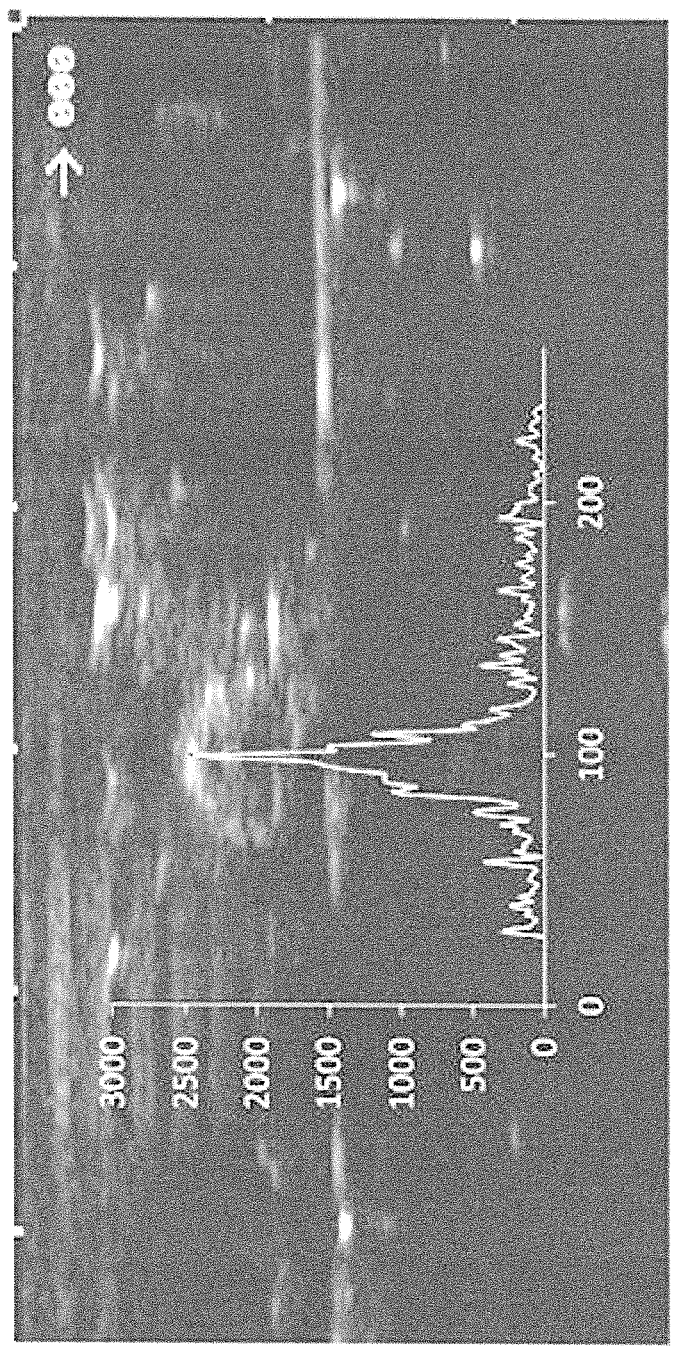
FIG. 18 shows an example of the fusion of the images of FIG. 17 using the best gamma profile, obtained with the method according to the present invention.

In FIG. 18 there is an example of the fusion of the images of FIG. 17 using the best gamma profile, obtained with the process according to the present invention.

FIG. 19 shows an example of an ultrasound image compared with three scintigraphic images corresponding to the three portions of the scintigraphic probe A, B, C obtained by the method of the present invention, in which the profile corresponding to the portion A differs from those corresponding to the portions B, C.

Figure 20:
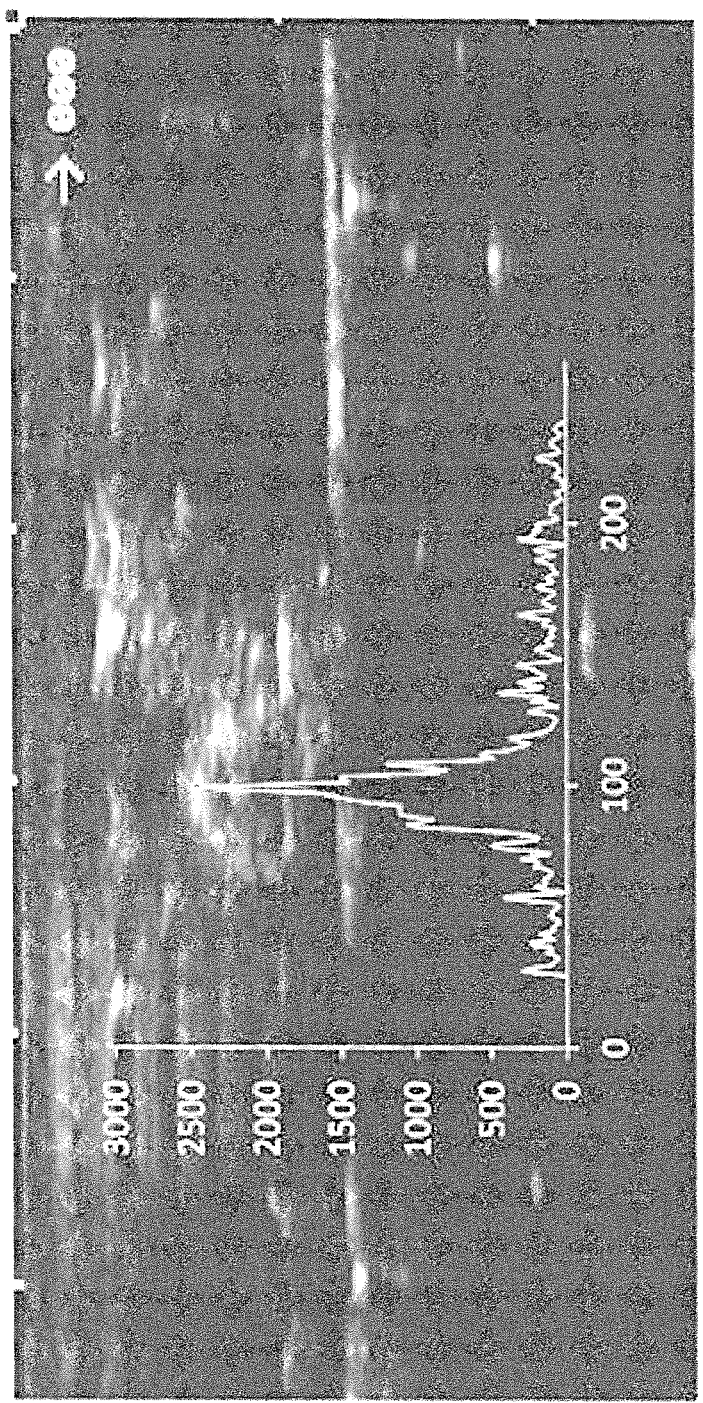
FIG. 20 shows an example of the fusion of the images of FIG. 19, using the best gamma profile, or the sum of the three profiles, obtained with the method according to the present invention.

FIG. 20 shows an example of fusion of the images of FIG. 19, using the best gamma profile, or the sum of the three profiles, obtained with the process according to the present invention.

If it happens that the three profiles are all non-homogeneous in terms of definition of the peak, the fact that one of them is more defined can give information about how to redirect the apparatus, because it intercepts a detection area different from those corresponding to the other profiles.

In addition, it is also possible to use the profile of the third zone C, in the case in which this profile differs from the corresponding profiles of the zones A and B, to subtract a background to the other two zones A and B, thus obtaining a better gamma image.

In these examples we see how the process according to the invention allows obtaining a unique image that presents both the ultrasound information and the scintigraphic one and allows the identification of pathological structures at a glance, greatly simplifying and improving the accuracy of diagnosis.

Advantages

As can it be seen from the above description and observation of the attached figures, the basic advantages of the present invention are clear, and are basically due to the idea of combining the information of scintigraphic images with the information of the ultrasound images.

The basic advantage of this invention is inherent in the application field of the echo-scintigraphic probe: screening, medical diagnostics, echo-radio-guided needle-biopsy, radio-guided surgery, lympho-scintigraphy, together with the guarantee of the same volume of vision obtainable by said individual medical applications, and with the added benefit of the merging of the two images (ultrasound and scintigraphic: the system gives a combined morphological and echographic image, together with the bio-distribution of the radiopharmaceutical), which takes place in real time exactly as summation or overlap of the same images, to date only obtainable separately and with certainly longer times. The latter is a rich and coveted information relating to characteristics inherent the functionality of the patient's body being examined.

Then, the echo-scintigraphic probe referred to in this invention can be considered equivalent in all respects to an ultrasound probe with the scintigraphic option, in analogy to what already realized with echographic detectors integrated with the Doppler (or color Doppler).

In essence, the fundamental advantage of the present invention is to be able to immediately get the ultrasound answer and, simultaneously, to obtain also the scintigraphic response relevant to the part of the anatomy that is, in the meantime, being observed by the ultrasound image. And this without the need, as in prior art, of sensors for the contextualization of the images. In fact, the device is such that to make the two probes integrally connected so as to have the same field of view, at least in one direction and the same center of image.

A further advantage of the present echo-scintigraphic probe is connected to its use, which does not provide for any additional dosimetric prescription. For the purposes of the dosimetric evaluation, the echo-scintigraphic probe has, in fact, the obvious advantage of not imparting "dose" increase to the radiological patient with respect to the traditional scintigraphic investigation.

Another added advantage is related to the "ancillarity" effect of the gamma image to the ultrasound image which are properly combined by the present echo-scintigraphic probe.

A further advantage of this invention is inherent in the practical handiness of the probe, which makes the performance of the service further faster (besides being of better quality) and gives hopes of success due to its use.

The echo-scintigraphic probe has the further advantage of also being further optimizable along time to obtain instant images, today already obtainable in a very short time, that is to say from very few seconds for the ultrasound image (<3 a) and 10-15 s for the scintigraphic image, thanks to equipment of the scintigraphic detector with SLIT collimator having a very high efficiency, achieving performance characteristics of about ten times larger than the average ones of scintigraphic systems of equivalent applications.

In conclusion, it is useful to reiterate that the purpose of obtaining a scintigraphic imaging in times compatible with echographic ones has been obtained, according to the present invention, by providing a SLIT collimator that, by providing a profile of the image of scintigraphic detection of the nodule (shown in figure), enables spatial resolution values compatible with ultrasound and detection efficiency such as to allow the acquisition of information in times comparable with ultrasound ones, thus maintaining unchanged the terms of use ultrasound, thus playing the role of perfect ancillarity.

In other words, the SLIT collimator and the resulting response, is the technological solution that allows full functionality of the apparatus according to the set objects.

Besides, being the two ultrasound and scintigraphic apparatus independent, the information capture is concurrent and this further minimizes the time of acquisition in the sense that the refresh rate of scintigraphic images may be further reduced (3/2) providing a "scout" image less precise (15% 20% error), but useful in the decisions of the operator in the processes of positioning of the probe.

The method of image fusion of the present invention then provides an instrument for the fusion of the images and for the operation of the probe. Thanks to the method of the invention, the comparison between the scintigraphic image and the ultrasound image is guaranteed with a very high accuracy, and constitutes a support to medical diagnostics.

LEGEND 1. echo-scintigraphic probe constituted by an ultrasound probe 11 inserted in the body 9 of the probe 1 and a gamma camera 3 in the tail 10 of the probe 1
2. I/O cables for the transmission of ultrasound signals
3. scintigraphic detector or gamma camera
3.1 first portion of the gamma camera
3.2 second portion of the gamma camera
4. scintillation crystal NaI:Tl
5. photomultiplier
6. lead screen
7. readout electronics of the gamma camera 3
8. probe head 1
9. probe body 1
10. handle or tail of the probe 1
11. ultrasound probe
12. probing end of the ultrasound probe 11
14. lead collimator of the gamma radiation
40. field of action of the scintigraphic probe
50. field of action of the ultrasound probe
A. first imaging area
B. second imaging area
C. third imaging area.

In the foregoing, the preferred embodiments have been described and variations of the present invention have been suggested, but it is to be understood that those skilled in the art can make other variations and changes, without so departing from the relevant scope of protection, as defined by the attached claims.

The invention claimed is:

1. An echo-scintigraphic probe for medical applications, comprising:

an echographic probe comprising a plurality of piezoelectric bands extended along an axis y and adjacent to one another along an axis x perpendicular to said y axis, said y axis defining the scanning direction of the echographic probe; and a scintigraphic probe for the detection of gamma rays, comprising:
a collimator;
a scintillation crystal with a scintillation crystal section on a section plane parallel to the two directions x and y and perpendicular to an axis z;
wherein the scintillation crystal, the collimator and the echographic probe are disposed in line, in the order along said z-axis, in such a way that they are integral with each other and such that:
the echographic probe constitutes an end of said echo-scintigraphic probe and is apt to contact, in use, a zone of biological tissue to be analysed;
the orthogonal projection of said echographic probe on said section plane overlaps said scintillation crystal section on an overlapping area smaller than or equal to the half of said scintillation crystal section; and
said echo-scintillation probe being characterized in that said collimator is a SLIT collimator with a plurality of collimation slits, and the piezoelectric bands of said plurality of piezoelectric bands are aligned to the collimation slits of said plurality of collimation slits.

2. The echo-scintigraphic probe according to claim 1, wherein said echographic probe is an echographic B-mode probe with quadrangular section perpendicular to said z-axis, the orthogonal projection of said quadrangular section onto said section plane overlapping said scintillation crystal section entirely along the direction x and partially along direction y for a portion not larger than its half.

3. The echo-scintigraphic probe according to claim 1, wherein said slit collimator presents slits with a length that is smaller than the dimension, in the direction of the same slits, of the scintillation crystal, the zone of the scintillation crystal outside the orthogonal projection of the collimator onto it being shielded with absorbing materials.

4. The echo-scintigraphic probe according to claim 1, further comprising, in line along said z-axis with the scintillation crystal and adjacent to it, a photo-detection system configured for the spatial sampling of the light distribution coming from the scintillation crystal.

5. The echo-scintigraphic probe according to claim 4, wherein said photo-detection system is a system with multiple detection elements or a system of small independent, semiconductor photo-detectors assembled into an array.

6. The echo-scintigraphic probe according to claim 4, comprising a handle including a detection and control electronics of the scintigraphic probe in a longitudinal portion of the echo-scintigraphic probe and in a line along said z-axis with the scintillation crystal and said photo-detection system.

7. The echo-scintigraphic probe according to claim 4 wherein said collimator is provided in a head portion of said echo-scintigraphic probe, the echographic probe being positioned in such a way to protrude with respect to said head portion.

8. The echo-scintigraphic probe according to claim 7, wherein laterally to said head portion and laterally to the photo-detection system a plurality of lead plates for the shielding against radiations is provided.

9. The echo-scintigraphic probe according to claim 1, wherein the slit collimator presents slats having thickness equal to 20-30 hundredths of mm, oriented along the y-axis and evenly spaced by 1-2 millimetres along the x-axis by means of a rigid synthetic foam, what has the effect of optimizing the obtaining of a perfectly linear scintigraphic image and, at the same time, maximising the efficiency of the echo-scintigraphic probe.

* * * * *